(12) United States Patent
Lazzari et al.

(10) Patent No.: US 8,106,218 B2
(45) Date of Patent: *Jan. 31, 2012

(54) PHARMACEUTICAL COMPOUNDS

(75) Inventors: Paolo Lazzari, Cagliari (IT); Stefania Ruiu, Cagliari (IT); Gerard Aime Pinna, Sassari (IT); Gabriele Murineddu, Sassari (IT)

(73) Assignee: Neuroscienze Pharmaness S.C. A R.L., Pula (IT)

( * ) Notice: Subject to any disclaimer, the term of this patent is extended or adjusted under 35 U.S.C. 154(b) by 339 days.

This patent is subject to a terminal disclaimer.

(21) Appl. No.: 12/330,434

(22) Filed: Dec. 8, 2008

(65) Prior Publication Data

US 2009/0081123 A1   Mar. 26, 2009

Related U.S. Application Data

(63) Continuation of application No. 11/134,502, filed on May 23, 2005, now Pat. No. 7,485,730.

(30) Foreign Application Priority Data

May 24, 2004 (IT) .............................. MI2004A1033

(51) Int. Cl.
  *A61K 31/4162* (2006.01)
  *C07D 495/04* (2006.01)
(52) U.S. Cl. .................... 548/359.5; 514/403
(58) Field of Classification Search ................ 548/359.5
See application file for complete search history.

(56) References Cited

U.S. PATENT DOCUMENTS

| | | | |
|---|---|---|---|
| 5,547,975 | A | 8/1996 | Talley et al. |
| 6,028,084 | A | 2/2000 | Barth et al. |
| 6,080,745 | A | 6/2000 | Davey et al. |
| 6,100,259 | A | 8/2000 | Xiang et al. |
| 2001/0053788 | A1 | 12/2001 | Lange et al. |
| 2003/0003145 | A1 | 1/2003 | Abramovici et al. |
| 2004/0127492 | A1* | 7/2004 | Vazquez et al. ............ 514/224.2 |

FOREIGN PATENT DOCUMENTS

| | | |
|---|---|---|
| EP | 0656354 | 6/1995 |
| EP | 1230222 | 8/2002 |
| EP | 1230244 | 8/2002 |
| WO | WO 01/32629 A1 | 5/2001 |
| WO | WO 01/32663 A2 | 5/2001 |
| WO | WO 03/070236 A2 | 8/2003 |
| WO | WO 03/070706 A1 | 8/2003 |
| WO | WO 2004/104007 A1 | 12/2004 |

OTHER PUBLICATIONS

Mussinu et al. (2003) Tricyclic Pyrazoles. Part 1: Synthesis and biological evaluation of novel 1,4-Dihydroindeno[1,2-c]pyrazol-based ligands for $CB_1$ and $CB_2$ cannabinoid receptors. Bioorganic & Medicinal Chemistry 11:251-263.

Franjo Grotenhermen, "Pharmacology of Cannabinoids", Neuroendocrinology Letters, vol. 25, vols. 1-2, pp. 14-23 (2004).
M.R. Pazos, et al., "Role of the endocannabinoid system in Alzheimer's disease: New perspectives", Life Sciences, 75, pp. 1907-1915 (2004).
Leo E. Hollister, "Health Aspects of Cannabis", Pharmacological Reviews, vol. 38, No. 1, pp. 1- 20 (1986).
Philip W. Wirth, et al., "Anti-Inflammatory Properties of Cannabichromene", Life Science, vol. 26, pp. 1991-1995, (1980).
Murielle Rinaldi-Carmona et al., "SR 144528, the First Potent and Selective Antagonist of the CB2 Cannabinoid Receptor", The Journal of Pharmacology and Experimental Therapeutics, vol. 284, No. 2, pp. 644-650 (1998).
Thompson et al., Current Medicinal Chemistry, Oct. 2002, 9(19), pp. 1751-1762.
CA Registry No. 727666-49-1, entry date into the Registry file on STN is Aug. 17, 2004.
D'Alessio et al., Bioorganic & Medicinal Chemistry Letters, 15, (Mar. 1, 2005), pp. 1315-1319.
Q. Lu et al., "Expression of CB2 cannabinoid receptor mRNA in adult rat retina", *Visual Neurosci*. 17, 91-95, 2000.
M. Glass, "The Role of Cannabinoids in Neurodegenerative Diseases", *Prog. Neoro-Psychopharmacol. & Biol. Psychiatri*. 25, 743-765, 2001.
A. Porcella et al., "Cannabinoid receptor CB, mRNA is highly expressed in the rat cilliary body; implications for the antiglaucoma properties of marihuana", *Molecular Brain Research* 58, 240-245, 1998.

(Continued)

*Primary Examiner* — Laura L. Stockton
(74) *Attorney, Agent, or Firm* — Womble Carlyle Sandridge & Rice, LLP

(57) ABSTRACT

Tricyclic pyrazole derivatives of the following formula (I) having affinity for the cannabinoidergic CB1 and/or CB2 receptors:

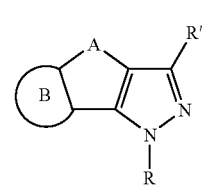

(I)

wherein:
  A represents a group selected from one of the following: $-(CH_2)_t-$, $-(CH_2)-S(O)_z-$, or $-S(O)_z-(CH_2)-$,
  B is a heteroaryl, optionally substituted;
  R is a group selected from the following:
    alkyl, aryl, arylalkyl or arylalkenyl, not substituted or having from one to four substituents, equal to or different from each other;
  R' is a group selected from the following:
    an ether group of formula $-(CH_2)-O-(CH_2)_v-R''$,
    a ketonic group of formula $-C(O)-Z'$, wherein Z' is as defined below;
    a substituent having an hydroxyl function of formula $-CH(OH)-Z'$;
    an amide substituent of formula $-C(O)-NH-T'$.

16 Claims, No Drawings

OTHER PUBLICATIONS

A. Porcella et al., "The human eye expresses high levels of CB1 cannabinoid receptor mRNA and protein", *European Journal of Neurosci.* 12, 1-5, 2000.

M Pacheco et al., "Aminoalkylindoles: Actions on Specific G-Protein-Linked Receptors", *j. Pharmacol. Exp. Ther.* 257, 170-183, 1991.

B.R. Martin et al., "Behavioral Biochemical, and Molecular Modeling Evaluations of Cannabinoid Analogs", *Pharmacol. Biochem. Behav.* 40, 471-478, 1991.

P.B. Smith et al., "The Pharmacological Activity of Anandamide, a Putative Endogenous Cannabinoid, in Mice", *J. Pharmacol. Exp. Ther.* 270, 219-227, 1994.

M. Rinaldi-Carmona et al., "SR141716A, a potent and selective antagonist of the brain cannabinoid receptor", *FEBS Lett.*, 350, 240-244, 1994.

Remington, "The Science and Practice of Pharmacy", 11, 1457, 1995.

H. Tanaka et al., "Synthesis and evaluation of novel 2-aryl-2,5,6,7-tetrahydro-3H-thienol[2',3':6,7]cycloheptal[1,2-c]pyridazin- -ones and 2-aryl-5,6-dihydrothienol[2,3-h]cinnoin-3(2H)-ones as anxiolytics", *Eur. J. Med. Chem.* 32, 607-615, 1997.

G.A. Pinna et al., "Synthesis and pharmacological evaluation of thienocinnolin-3-(2H)-ones, bioisosters of antihypertensive and antithrombotic benzo(h)cinnolinones", *Eur. J. Med. Chem.* 29, 447-454, 1994.

G.A. Pinna et al., "Addition Reactions of Acetylenic Esters Upon 1-(2-Thienyl)- and 1-(3-Thienyl)-Ethanone Oximes and Upon 6,7-Dihydrobenzo(b)Thiophen-4(5H)-One and 5,6-Dihydrobenzo(b)Thiophen-7(4H)One Oximes, Formation of 2-(Thienyl)-Pyrroles and 4,5-Dihydro-1H-Thieno(g)Indoles", *British Library—Paper E/2/06335B*, 1279-1296, 1992.

G.A. Pinna et al., *J. Chem. Res.*, 1273-1281, 1993.

W.M. Rawls et al., "CB1 Receptors in the Preoptic Anterior Hypothalamus Regulate WIN 55212-2 [(4,5-Dihydro-2-methyl-4(4-morpholinylmethyl)-1-(1-naphthalenyl-carbonyl)-6H-pyrrolo[3,2,1ij]quinolin-6-one)]-Induced Hypothermia", *J. Pharmacol. Exp. Ther.* 303, 395-402, 2002.

R.G. Pertwee, "Further evidence for the presence of cannabinoid CB1, receptors in guinea-pig small intestine", Br. J. Pharmacol. 118, 2199-2205—1996.

G. Colombo et al., "Cannabinoid modulation of intestinal propulsion in mice", Eur. J. Pharmacol. 344, 67-69, 1998.

M.A. Casu et al. "Differential distribution of functional cannabinoid CB1 receptors in the mouse gasstroenteric tract", *Eur. J. Pharmacol.* 459, 97-105, 2003.

Y. Nagakura et al., Compounds possessing 5-HT3 receptor antagonistic activity inhibit intestinal propulsion in mice, *Eur. J. Pharmacol.* 311, 67-72, 1996.

\* cited by examiner

PHARMACEUTICAL COMPOUNDS

CROSS-REFERENCE TO RELATED APPLICATIONS

This application is a continuation of and claims the benefit under 35 U.S.C. §120 of U.S. application Ser. No. 11/134,502 filed May 23, 2005 which is hereby incorporated in its entirety by reference. This application and U.S. application Ser. No. 11/134,502 claim the benefit of Italian Patent Application No. MI 2004 A 001033, filed on May 24, 2004, in the Italian Patent and Trademark Office, the disclosure of which is incorporated herein in its entirety by reference.

DETAILED DESCRIPTION

The present invention relates to pyrazole tricyclic derivatives having affinity for cannabinoidergic CB1 and/or CB2 receptors, to the corresponding solvates and pharmaceutically acceptable salts and to their pharmaceutical compositions.

More specifically the present invention relates to pyrazole tricyclic derivatives having affinity for peripheric cannabinoidergic CB1 and/or CB2 receptors; said derivatives are indeed unable as such to pass the hemato-encephalic barrier. The compounds of the present invention are therefore usable in those pathologies wherein a therapeutic response is required depending on the activation of said peripheral receptors, without the appearance of any substantial side effects on the central nervous system. The tricyclic pyrazole derivatives of the present invention therefore show selectively their pharmacological activity on the peripheral system, without substantially causing any side effect on the central nervous system.

Cannabinoids are compounds deriving from sativa Cannabis, commonly known as marijuana. Among the at least 66 cannabinoid compounds characterizing the marijuana, tetrahydrocannabinols (THC) and $\Delta^9$-tetrahydrocannabinol ($\Delta^9$-THC) in particular, are considered as the most active. The properties which have indeed led to the use of marijuana as therapeutic agent of natural origin in mammalians and in men have been connected to the above compounds. Said properties are the following: the analgesic effect, the antiinflammatory activity, the reduction of the blood and intraocular pressure, the antiemetic activity. The negative effects which are associated to the marijuana use have furthermore been correlated to tetrahydrocannabinols, with particular reference to the psychological distortion of the perception, to the motor coordination loss, to the euphory, to the sedative effect. The cannabinoid pharmacological action appears directly correlated to their affinity towards two different classes of specific receptors belonging to the "G protein-coupled" receptor family; CB1 receptors, located in the central nervous system besides in the peripheral tissues, and CB2 receptors, identified in the cerebellum (Q. J. Lu et al.; *Visual Neurosci.*; 2000, 17, 9, 1-95) but which mainly find in the peripheral tissues (M. Glass; *Progr. Neuro-Psychopharmacol. & Biol. Psychiat.*; 2001, 25, 743-765). In the brain, the CB1 receptors are largely expressed in the hippocampus, in the cortical regions, in the cerebellum and inside the basal ganglia. Among the peripheral tissues wherein the CB1 receptors have been located, we remember testicles, small intestine, bladder, deferent duct. The CB1 receptors have furthermore been identified in the rat eye and in the human eye, in the retina and in the iris and in the ciliary body (A. Porcella et al.; *Molecular Brain Research*; 1998, 58, 240-245; A. Porcella et al.; *European Journal of Neuroscience*; 2000, 12, 1123-1127). The CB2 receptors are instead mainly located in the marginal spleen zones, in tonsils, besides in several immune system cells, as macrophages, monocytes, cells of the bone marrow, of thymus and pancreas. Other immune system cells wherein the CB2 receptors are significantly present are the T4 and T8 cells, the polymorphonucleate leucocytes, in particular the cells called natural killers and lymphocytes B.

The compounds capable to interact, as agonists or antagonists, with the CB2 receptors can therefore be used in the treatment of diseases wherein immune system cells or immune disorders are involved. The activation (modulation) of the CB2 receptors is also important in the treatment of other diseases, as for example in the osteoporosis, renal ischemia treatment and in inflammatory states.

The compounds with affinity towards the CB1 receptors can be used in the treatment of eye-diseases as glaucoma, lung-diseases as asthma and chronic bronchitis, inflammations as for example arthritis, allergies and allergic reactions as for example allergic rhinitis, contact dermatitis, allergic conjunctivitis. Such compounds can also be used in the pain treatment, in anxiety cases, in mood problems, delirium states, psychotic afflictions in general, besides for schizophrenia, depression treatment and when abuse and/or dependency substances are used (for example alcoholism and tabagism). The same compounds can also be used to contrast vomit, nausea, giddiness, especially in case of patients submitted to chemotherapy; in the treatment of neuropathies, hemicrania, stress, psychosomatic origin diseases, epilepsy, Tourette syndrome, Parkinson disease, Huntington disease, Alzheimer disease, senile dementia, and in case of cognitive disease and of memory loss.

Further applications of the compounds having affinity towards CB1 receptors are the treatment of pathologies related to the appetite (obesity, bulimia), pathologies of the gastrointestinal tract and of the bladder, cardiovascular diseases, urinary and fertility problems, neuroinflammatory pathologies as for example multiple sclerosis, Guillain-Barré syndrome, viral encephalitis. For example some CB1 agonist active principles are successfully used in the nausea and vomit treatment associated to the chemotherapy and in the appetite stimulation in AIDS' patients. Compounds with antagonist activity towards CB1 receptors can be used for example in the treatment of psychosis, anxiety, depression, schizophrenia, obesity, neurological diseases (for example dementia, Parkinson disease, Alzheimer disease, epilepsy, Tourette syndrome), in memory loss, in the pain treatment, in central nervous system disease involving the neurotransmission of cannabinoids, in the treatment of gastrointestinal and/or cardiovascular troubles.

In connection with the wide cannabinoid pharmacological applications, over the last years several studies have been started to find endocannabinoids and for the synthesis of new compounds capable to selectively interact towards the two subclasses of cannabinoidergic CB1 and CB2 receptors. The researches have led on the one hand to the identification of anandamide endocannabinoids (arachidonyl ethanolamide) and 2-arachidonyl glycerol, on the other hand to the obtainment of different classes of synthesis compounds, agonists or antagonists towards the CB1 or CB2 receptors.

The class of the compounds having agonist activity towards the CB1 receptors (cannabimimetic activity) comprises synthesis compounds having a base structure directly derived from that of $\Delta^9$-THC, as (−)-11-OH-$\Delta^8$THC-dimethylheptyl (HU210) and nabilone, and compounds structurally different from $\Delta^9$-THC, as aminoalkylindols of the WIN 55,212-2 series (M. Pacheco et al.; *J. Pharmacol. Exp. Ther.*; 1991, 257, 1701-183) or as bicyclic cannabinols (non classic cannabinoids) referring to the compound CP 55,940 (M. Glass; *Progr. Neuro-Psychopharmacol. & Biol. Psychiat.;* 2001, 25, 743-765). The compounds having cannabimimetic activity show in vivo the following effects: hypoactivity, hypothermia, analgesia and catalepsy (B. R. Martin et al.; *Pharmacol. Biochem. Behav.;* 1991, 40, 471-478; P. B. Smith et al.; *J. Pharmacol. Exp. Ther.;* 1994, 270, 219-227).

Another class of synthesis compounds which have shown themselves particularly similar and selective towards cannabinoidergic receptors is that of the 3-pyrazole carboxylic acid derivatives. The reference compound of this class of derivatives is commonly indicated with the abbreviation SR141716A: [N-piperidino-5-(4-chlorophenyl)-1-(2,4-dichlorophenyl)-4-methylpyrazol-3-carboxyamide], described in EP 656,354. In particular the SR141716A compound has shown the following properties: a high affinity for the CB1 receptors (Ki=1.98±0.36 nM), a significant selectivity towards the CB1 receptors (affinity towards the CB1 receptors about a thousand times higher than that for the CB2 receptors), capability of inhibiting the cannabinoid activity, therefore antagonist activity, in samples in vivo and in vitro (M. Rinaldi-Carmona et al.; *FEBS Lett.;* 1994, 350, 240-244). On the basis of the properties pointed out, besides of several clinical and preclinical studies, the SR141716A compound, lately renamed by Sanofi-Synthélabo Rimonabant®, is designed to be mainly used as antihunger active principle in the obesity treatment as well as in the tabagism treatment.

Patent application US 2001/0053788 describes 4,5-dihydro-1H-pyrazole compounds as potential antagonists of the CB1 receptors. The general formula of the claimed compounds is reported hereinafter:

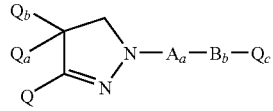

wherein: Q, $Q_a$, $Q_b$, $Q_c$, $A_a$, $B_b$ have different meanings.

Compounds having high affinity for the cannabinoidergic receptors and, especially, high selectivity for the CB1 receptors, are described in EP 1,230,244. In particular, said compounds are tricyclic analogues of SR141716A having general structure;

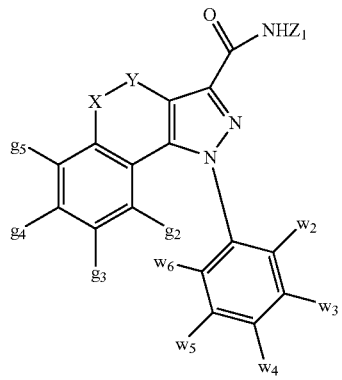

wherein $Z_1$, $w_2$, $w_3$, $w_4$, $w_5$, $w_6$, $g_2$, $g_3$, $g_4$, $g_5$ have different meanings; X—Y— represent a group selected from: —(CH$_2$)$_r$—CH$_2$—, —CH$_2$—S(O)$_p$—, —S(O)$_p$—CH$_2$—, with r equal to 1 or 2, p equal to zero, 1 or 2. Compounds having high affinity for the cannabinoidergic receptors and, above all, high selectivity for CB2 receptors, are described in EP 1,230,222. In particular, the compounds described in this patent are tricyclic analogues of SR141716A having general structure:

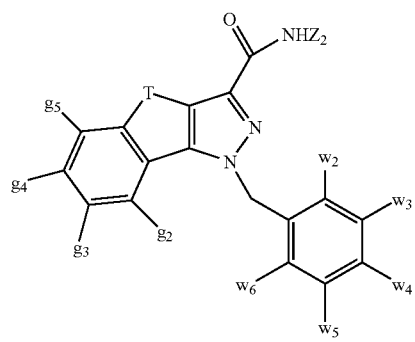

wherein: -T- represents a —(CH$_2$)$_m$— group, with m equal to 1 or 2; $Z_2$, $w_2$, $w_3$, $w_4$, $w_5$, $w_6$, $g_2$, $g_3$, $g_4$, $g_5$ have different meanings.

Other compounds having a pyrazole structure capable to modulate the CB2 receptors are described in U.S. Pat. No. 6,100,259 and are represented by the general formula:

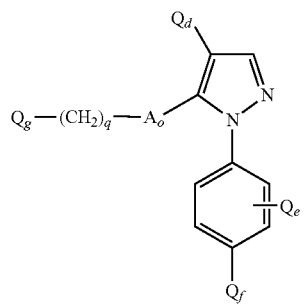

wherein q is between 1 and 6, while $A_o$, $Q_d$, $Q_e$, $Q_f$, $Q_g$ have different meanings.

A further compound having a pyrazole structure with affinity and selectivity towards CB2 receptors is the compound known with the abbreviation SR144528 (M. Rinaldi-Carmona et Al. J. Pharmacol. Expt. Ther. 1998 284 644-650) the structure of which is reported hereinafter:

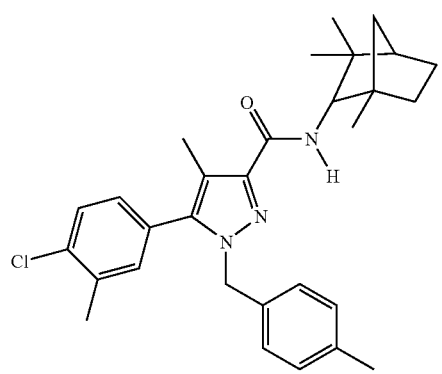

Another compound known for its selectivity towards the CB2 receptors, having agonist activity towards this subclass of receptors, is the compound 1-propyl-2-methyl-3-naphthoyl-indole, called JWH-015 (M. Glass; *Progr. Neuro-Psychopharmacol. & Biol. Psychiat.;* 2001, 25, 743-765).

As said, the above patents and publications describe compounds exerting their therapeutical activity by activating the CB1 and/or $CO_2$ receptors, but they do not give any indication as to the fact that such active principles have the property not to pass the hematoencephalic barrier, therefore that they are active only at a peripheral level.

The need was felt to have available compounds having affinity for the cannabinoidergic CB1 and/or CB2 receptors, capable to selectively act at a peripheral level, without substantial effects on the central nervous system.

An object of the present invention are tricyclic pyrazole derivatives of formula (I) having affinity for the cannabinoidergic CB1 and/or CB2 receptors:

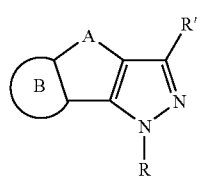

(I)

wherein:
A represents a group selected from one of the following:
—$(CH_2)_t$—, —$(CH_2)$—$S(O)_z$—, or —$S(O)_z$—$(CH_2)$—, wherein:
t is equal to 1, 2 or 3;
z is equal to 0, 1 or 2;
B is a heteroaryl, optionally substituted depending on the atom number of the ring with a number of substituents ranging from 1 to 4, equal to or different from each other, selected from: halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, isothiocyanate, phenyl, cycloalkyl, saturated or unsaturated heterocycle, heteroaryl;
R is a group selected from the following:
linear or branched $C_1$-$C_{10}$ alkyl, wherein the end of the main chain not linked to the nitrogen atom has —$CH_2$—W termination, W being a group selected from hydrogen, halogen, isothiocyanate, CN, OH, $OCH_3$, $NH_2$, —CH—$CH_2$;
aryl, arylalkyl or arylalkenyl, not substituted or having from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle, phenyl;
R' is a group selected from the following:
an ether group of formula: —$(CH_2)$—O—$(CH_2)_v$—R", wherein:
v is an integer equal to 1 or 2;
R" is a saturated or unsaturated heterocycle as defined below, or a $C_3$-$C_{15}$ cycloalkyl, or an aryl, or a heteroaryl as defined below;
a ketonic group of formula —C(O)—Z', wherein Z' is a $C_1$-$C_8$ alkyl or a $C_3$-$C_{15}$ cycloalkyl, a saturated or unsaturated heterocycle as defined below, or an aryl, or a heteroaryl;

a substitutent having an hydroxyl function of formula —CH(OH)—Z', Z' being as above;
an amidic substituent of formula —C(O)—NH-T', T' being a group selected from:
$C_1$-$C_8$ alkyl;
$C_1$-$C_7$ haloalkyl;
aryl, arylalkyl or arylalkenyl as defined below, optionally containing one heteroatom selected among S, N, O, not substituted or optionally having from one to five substituents, said substituents equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy;
a $C_3$-$C_{15}$ cycloalkyl not substituted or substituted with one or more $C_1$-$C_7$ alkyl chains, said chains being from one to four for $C_5$-$C_{15}$ cycloalkyls, being from one to three for the $C_4$ cycloalkyl, being from one to two for the $C_3$ cycloalkyl, said alkyl groups being equal to or different from each other;
a group having formula:

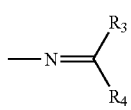

(IA)

wherein $R_3$ and $R_4$ equal to or different from each other, represent hydrogen or $C_1$-$C_3$ alkyl, with the proviso that $R_3$ and $R_4$ are not both hydrogen;
a group having formula:

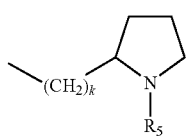

(IB)

wherein $R_5$ represents a $C_1$-$C_3$ alkyl and k is an integer between 1 and 3;
a group $NR_1R_2$, wherein $R_1$ and $R_2$, equal or different, have the following meanings:
hydrogen;
$C_1$-$C_7$ alkyl;
aryl, arylalkyl or arylalkenyl not substituted or optionally having on the aromatic rings from one to five substituents, equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy;
or $R_1$ and $R_2$ together with the nitrogen atom to which they are linked form a, saturated or unsaturated, heterocycle from 5 to 10 carbon atoms, not substituted or optionally having from one to four substituents, equal to or different from each other, selected from $C_1$-$C_7$ alkyl, phenyl, benzyl, said phenyl or benzyl optionally substituted with one or more groups, equal to or different from each other, selected from: halogen, $C_1$-$C_7$ alkyl, $C_1$-$C_7$ haloalkyl, $C_1$-$C_7$ haloalkoxy, $C_1$-$C_7$ alkylthio, $C_1$-$C_7$ alkoxy.
Where not otherwise specified, in the whole text:
the term "alkyl" means a $C_1$-$C_{20}$ saturated hydrocarbon chain linear or branched when possible;

the term "alkenyl" means a $C_2$-$C_{20}$ mono- or polyunsaturated, preferably mono-unsaturated, hydrocarbon chain, linear or branched when possible;

the term "cycloalkyl" means an aliphatic monocyclic ring, for example from 3 to 8 carbon atoms, in particular from 4 to 6 carbon atoms, and a polycyclic structure from 8 to 19 carbon atoms; wherein the ring or the rings do not contain unsaturations;

the term "saturated heterocycle" means a cycloalkyl as above wherein at least one carbon atom is substituted by one heteroatom selected from S, O, N; when the ring is monocyclic, preferably the heteroatoms are no more than 2;

the term "unsaturated heterocycle" means a cycloalkyl as above having one or more double bonds, with the proviso that the structure does not result of aromatic type, wherein at least one carbon atom is substituted by one heteroatom selected from S, O, N;

the term "halogen" indifferently indicates one atom selected from fluorine, chlorine, bromine, iodine;

the term "haloalkyl" means an alkyl according to the above definition, wherein one or more hydrogen atoms are substituted by as many halogen atoms; for example trifluoromethyl, 1-bromo-n-butyl, pentachloroethyl;

the term "aryl" means a $C_6$ monocyclic aromatic radical, or a $C_8$-$C_{19}$ polycyclic radical wherein at least one ring is aromatic, exclusively containing carbon atoms and hydrogen atoms;

the term "heteroaryl" means an aryl as above, except that the monocyclic radical is $C_5$-$C_6$ wherein at least one carbon atom is substituted by one heteroatom selected from S, O, N; preferably the heteroatoms in case of monocyclic radicals are no more than 2;

the term "arylalkyl" means an alkyl as above, preferably $C_1$-$C_7$, linked to an aryl as above, for example benzyl;

the term "arylalkenyl" means an alkenyl as above linked to an aryl as above;

with "compound having affinity towards the receptors" it is meant a compound which has in vivo agonist, or antagonist, or partial agonist, or partial antagonist, or opposite agonist, or opposite antagonist, or opposite partial agonist activity towards receptors. The meaning of such terms is well known to the skilled man in the field.

The preferred compounds of formula (I) are those wherein:

A is —$(CH_2)_t$—, wherein t is as above;

B is an heteroaryl with ring having 5 or 6 atoms, optionally substituted, depending on the atom number of the ring, with a number of substituents ranging from 1 to 4, said substituents equal to or different from each other, selected from the following: halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy;

R has the following meanings:
  a linear or branched $C_1$-$C_{10}$ alkyl, wherein the end of the main chain not linked to the nitrogen atom has —$CH_2$—W termination, W being a halogen;
  an arylalkyl or an arylalkenyl not substituted or containing from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle, phenyl;

R' is selected from the following groups:
  amide of formula —C(O)—NH-T' wherein T' has the meanings reported above for formula (I), excluding the formulas (IA) and (IB).

The compounds of formula (I) are still more preferred, wherein:

A is —$(CH_2)_t$—, wherein t is as above;

B is an heteroaryl selected from the following: thiophene, pyridine, furan, oxazole, thiazole, imidazole, pyrazole, isoxazole, isothiazole, triazole, pyridazine, pyrimidine, pyrazine, triazine, pyrrole; said heteroaryls optionally substituted with one, two, three or four substituents, equal to or different from each other, selected from the following: halogen, $C_1$-$C_3$ alkyl, $C_1$-$C_3$ alkylthio, $C_1$-$C_3$ alkoxy, $C_1$-$C_3$ haloalkyl, $C_1$-$C_3$ haloalkoxy; preferably the heteroaryls with ring having 5 atoms are used, still more preferably the heteroaryl is thiophene;

R has the following meanings:
  linear or branched $C_1$-$C_7$ alkyl, wherein the end not linked to the nitrogen atom of the main chain has —$CH_2$—W termination, W being a halogen;
  arylalkyl or an arylalkenyl, not substituted or having from one to five substituents, equal to or different from each other, selected from halogen, $C_1$-$C_3$ alkyl, $C_1$-$C_3$ alkylthio, $C_1$-$C_3$ alkoxy, $C_1$-$C_3$ haloalkyl, $C_1$-$C_3$ haloalkoxy;

R' is selected from the following groups:
  amidic group of formula —C(O)—NH-T', wherein T' is a group selected from the following groups:
    $C_1$-$C_7$ alkyl;
    $C_1$-$C_7$ haloalkyl;
    aryl, arylalkyl or arylalkenyl, optionally containing one heteroatom, selected from N, S, O, not substituted or having from one to five substituents, equal to or different from each other, selected from halogen, $C_1$-$C_3$ alkyl, $C_1$-$C_3$ haloalkyl, $C_1$-$C_3$ haloalkoxy, $C_1$-$C_3$ alkylthio, $C_1$-$C_3$ alkoxy;
    one group $NR_1R_2$, wherein $R_1$ and $R_2$ have the above values in formula (I);
    a $C_3$-$C_{15}$ cycloalkyl not substituted or substituted with one or more $C_1$-$C_7$ alkyl chains, said chains being from one to four for $C_5$-$C_{15}$ cycloalkyls, being from one to three for the $C_4$ cycloalkyl, being from one to two for the $C_3$ cycloalkyl, said alkyl groups being equal to or different from each other.

Preferably the compounds of formula (I) are used, wherein R'=—C(O)—NH-T', T' being as defined above.

Examples of said compounds are the following:

N-piperidinyl-7-chloro-1-(2',4'-dichlorophenyl)-4,5-dihydro-1H-thieno[2,3-g]indazol-3-carboxamide;

N-homopiperidinyl-7-chloro-1-(2',4'-dichlorophenyl)-4,5-dihydro-1H-thieno[2,3-g]indazol-3-carboxamide;

N-pyrrolidinyl-7-chloro-1-(2',4'-dichlorophenyl)-4,5-dihydro-1H-thieno[2,3-g]indazol-3-carboxamide;

N-piperidinyl-7-bromo-1-(2',4'-dichlorophenyl)-4,5-dihydro-1H-thieno[2,3-g]indazol-3-carboxamide;

N-homopiperidinyl-7-bromo-1-(2',4'-dichlorophenyl)-4,5-dihydro-1H-thieno[2,3-g]indazol-3-carboxamide;

N-pyrrolidinyl-7-bromo-1-(2',4'-dichlorophenyl)-4,5-dihydro-1H-thieno[2,3-g]indazol-3-carboxamide;

N-piperidinyl-7-methyl-1-(2',4'-dichlorophenyl)-4,5-dihydro-1H-thieno[2,3-g]indazol-3-carboxamide;

N-homopiperidinyl-7-methyl-1-(2',4'-dichlorophenyl)-4,5-dihydro-1H-thieno[2,3-g]indazol-3-carboxamide;

N-pyrrolidinyl-7-methyl-1-(2',4'-dichlorophenyl)-4,5-dihydro-1H-thieno[2,3-g]indazol-3-carboxamide;

N-piperidinyl-7-chloro-1-(2',4'-dichlorophenyl)-4,5-dihydro-1H-thieno[3,2-g]indazol-3-carboxamide;

N-piperidinyl-6-bromo-1-(2',4'-dichlorophenyl)-4,5-dihydro-1H-thieno[3,2-g]indazol-3-carboxamide;

N-piperidinyl-6-bromo-7-chloro-1-(2',4'-dichlorophenyl)-4,5-dihydro-1H-thieno[3,2-g]indazol-3-carboxamide;
N-piperidinyl-8-chloro-1-(2",4"-dichlorophenyl)-1,4,5,6-tetrahydrothieno[2',3':6,7]cyclohepta[1,2-c]pyrazol-3-carboxamide;
N-piperidinyl-8-bromo-1-(2',4'-dichlorophenyl)-1,4,5,6-tetrahydrothieno[2',3':6,7]cyclohepta[1,2-c]pyrazol-3-carboxamide;
N-piperidinyl-8-chloro-1-(2",4"-dichlorophenyl)-1,4,5,6-tetrahydrothieno[3',2':6,7]cyclohepta[1,2-c]pyrazol-3-carboxamide;
N-piperidinyl-8-bromo-1-(2",4"-dichlorophenyl)-1,4,5,6-tetrahydrothieno[3,2':6,7]cyclohepta[1,2-c]pyrazol-3-carboxamide;
N-piperidinyl-6-methyl-1-(2",4"-dichlorophenyl)-1,4-dihydrothieno[2',3':4,5]cyclopenta[1,2-c]pyrazol-3-carboxamide;
N-piperidinyl-6-methyl-1-(2",4"-dichlorophenyl)-1,4-dihydrothieno[3',2':4,5]cyclopenta[1,2-c]pyrazol-3-carboxamide.

The compounds of formula (I) of the present invention depending on the substituents can contain chiral centres in their structure.

All the various isomers and the corresponding mixtures are considered included in the present invention. In the compounds of formula (I) cis-trans type isomers can also be present.

The Applicant has surprisingly and unexpectedly found that the compounds of formula (I) have affinity for the cannabinoidergic CB1 and/or CB2 receptors and are capable to selectively act at a peripheral level, without effects on the central nervous system, which could cause undesired side effects. For example the compound of the Example 3.6 (see the Examples of the present invention) has resulted active towards the CB1 and CB2 receptors and therefore can be used for the treatment of pathologies of the gastroenteric tract or in the case of immune disorders. Said compound is not capable to pass the hemato-encephalic barrier, and therefore selectively exerts its activity at a peripheral level and its use therefore does not imply undesired side effects on the central nervous system.

The above defined hydrates, solvates and pharmaceutically acceptable salts of the compounds of formula (I), comprising all the various isomers and the corresponding mixtures, are a further object of the present invention.

The meaning of the terms "hydrate" and "solvate" is well known to the skilled man in the field.

A further object of the present invention is a process for preparing the compounds of general formula (I) wherein R' has the above meanings, comprising:
i) synthesis of the acid of the following general formula (II), or optionally of one of its reactive derivatives, selected from acyl halides, anhydrides, mixed anhydrides, imidazolides, ester-amide adducts, linear or branched $C_1$-$C_4$ alkyl esters:

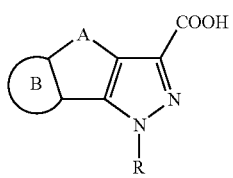

comprising the following steps:
obtainment of α-hydroxy-γ-ketoesters of formula (IV), wherein A, B are as previously defined, starting from a compound of formula (III) by reaction with sodium alkoxide (RONa) and diethyloxalate in $C_1$-$C_3$ alcoholic solvent under reflux (Claisen condensation):

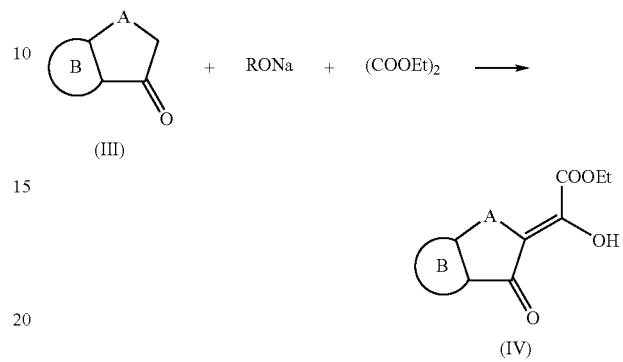

reaction of the compounds of formula (IV) with an hydrazine of formula (V) wherein R is as previously defined, said compound (V) being optionally under the form of a hydrochloride salt in alcoholic solvent or in acetic acid under reflux, to obtain the tricyclic compound of formula:

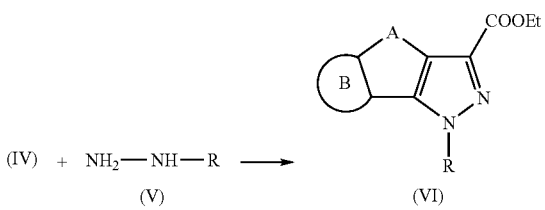

basic hydrolysis with alkaline hydroxides in hydroalcoholic solution of the compound of formula (VI) under reflux to obtain the acid of general formula (II);
optionally, formation of a reactive derivative of the acid of general formula (II), as defined above;
ii) when in the general formula R'=—(CH$_2$)—O—(CH$_2$)$_v$—R", wherein R" is as above, the compounds of formula (I) can be prepared starting from the acid of formula (II) or from one of its esters, preferably the ethyl ester, which is reduced in a first step, by operating at room temperature, into a primary alcohol in a solvent inert under the reaction conditions (for example tetrahydrofuran), for example by using an organic metal hydride, for example di-isobutyl aluminum hydride (DIBAL-H), or the lithium and aluminum hydride LiAlH$_4$; then the obtained primary alcohol is reacted at room temperature with an alkyl halide of formula R"—(CH$_2$)Hal, wherein Hal=halogen, in the presence of an alkaline hydride, for example sodium hydride, to obtain the above compounds, wherein R'=—(CH$_2$)—O—(CH$_2$)$_v$—R".

When in the general formula (I) R'=—C(O)—Z', wherein Z' is as above, the compounds of formula (I) can be prepared according to one of the following methods:
by reacting an ester of the acid of general formula (II), preferably the ethyl ester with trialkylaluminum, preferably Al(CH$_3$)$_3$ with a hydrochloride salt of an amine, the amine being hydrochloride salt preferably HN(OCH$_3$)CH$_3$.HCl in a solvent inert under the reaction conditions, preferably dichloromethane, initially at 0° C., then at room temperature until the ester disappearance; then adding at 0° C. to the reaction mixture Z'MgBr, wherein Z' is as above, and allowing to react at room temperature until obtaining the compound of formula (I) wherein R'=—C(O)—Z';

by reacting the acid of formula (II), or one of its reactive derivatives, with an organic metal salt of formula Z'⁻Me⁺ wherein Me⁺ is preferably an alkaline metal cation for example lithium, in a solvent inert under the reaction conditions, obtaining the compound of formula (I) wherein R'=—C(O)—Z'.

The former of the two above processes is preferably used.

When in the general formula (I) R'=—CH(OH)—Z', wherein Z' is as above, the synthesis is carried out in two steps:

preparation of the compound of formula (I) wherein R'=—C(O)—Z' by using one of the two reactions reported above;

reaction of the compound of formula (I) wherein R'=—C(O)—Z' with lithium and aluminum hydride or sodium borohydride at room temperature to give the final product of formula (I) wherein A=—CH(OH)—Z'.

When in the general formula (I) R'=—C(O)—NH-T', wherein T' is as above, the compounds are prepared by reacting in a solvent inert under the reaction conditions of the acid of formula (II) in the form of a corresponding reactive derivative as above, at room temperature with a compound of general formula:

(VII)

wherein T' has the previously defined meanings.

The compounds of formula (III) and (VII) are available on the market or are described in the concerned publications. Preferred examples of acids of formula (II) comprise:

7-chloro-1-(2',4'-dichlorophenyl)-4,5-dihydro-1H-thieno[2,3-g]indazol-3-carboxylic acid;
7-bromo-1-(2',4'-dichlorophenyl)-4,5-dihydro-1H-thieno[2,3-g]indazol-3-carboxylic acid;
7-methyl-1-(2',4'-dichlorophenyl)-4,5-dihydro-1H-thieno[2,3-g]indazol-3-carboxylic acid;
7-chloro-1-(2,4'-dichlorophenyl)-4,5-dihydro-1H-thieno[3,2-g]indazol-3-carboxylic acid;
6-bromo-1-(2',4'-dichlorophenyl)-4,5-dihydro-1H-thieno[3,2-g]indazol-3-carboxylic acid;
6-bromo-7-chloro-1-(2',4'-dichlorophenyl)-4,5-dihydro-1H-thieno[3,2-g]indazol-3-carboxylic acid;
8-chloro-1-(2",4"-dichlorophenyl)-1,4,5,6-tetrahydro thieno[2',3':6,7]cyclohepta[1,2-c]pyrazol-3-carboxylic acid;
8-bromo-1-(2",4"-dichlorophenyl)-1,4,5,6-tetrahydro thieno[2',3':6,7]cyclohepta[1,2-c]pyrazol-3-carboxylic acid;
8-chloro-1-(2",4"-dichlorophenyl)-1,4,5,6-tetrahydro thieno[3',2':6,7]cyclohepta[1,2-c]pyrazol-3-carboxylic acid;
8-bromo-1-(2",4"-dichlorophenyl)-1,4,5,6-tetrahydro thieno[3',2':6,7]cyclohepta[1,2-c]pyrazol-3-carboxylic acid;
6-methyl-1-(2",4"-dichlorophenyl)-1,4-dihydro thieno[2',3':4,5]cyclopenta[1,2-c]pyrazol-3-carboxylic acid;
6-methyl-1-(2",4"-dichlorophenyl)-1,4-dihydro thieno[3',2':4,5]cyclopenta[1,2-c]pyrazol-3-carboxylic acid.

With pharmaceutically acceptable salts all the salts are meant obtained by treating the compounds of formula (I) with organic or inorganic acids acceptable from the pharmaceutical point of view. For example hydrochlorides, sulphates, fumarates, oxalates, citrates, hydrogensulphates, succinates, paratoluensulphonates can be mentioned. See the volume: "Remington, The Science and Practice of Pharmacy", vol. II, 1995, page 1457.

A further object of the present invention is represented by the pharmaceutical compositions containing the compounds of general formula (I), comprising the isomers and their mixtures, the corresponding hydrates or solvates or pharmaceutically acceptable salts. Optionally said compositions contain additives or excipients capable to allow the compounds of formula (I) to pass the hemato-encephalic barrier.

With pharmaceutical compositions preparations are meant wherein the active principles of formula (I) (comprising all the different isomers and the corresponding mixtures), or the corresponding hydrates or solvates or pharmaceutically acceptable salts, are mixed with excipients, carriers, dyes, preservatives, flavorings and other additives the use of which is known in the pharmaceutical field.

The pharmaceutical compositions of the present invention can be administered by os, subcutaneous, sublingual, intramuscular, intravenous, topical, transdermal, rectal, ophthalmic, intranasal route. Said pharmaceutical compositions comprise for example dispersions, solutions, emulsions, microemulsions, powders, capsules, aerosol, suppositories, tablets, syrups, elixir, creams, gels, ointments, plasters.

The pharmaceutical compositions of the present invention can be obtained according to known methods of the pharmaceutical technique. For example, said pharmaceutical compositions can be obtained according to the processes indicated in U.S. Pat. No. 6,028,084, herein incorporated by reference.

The pharmaceutical compositions can also be prepared by using the methods and the additives indicated in patent application US2003/0003145. In these formulations sodium alkylsulphate or another surfactant commonly utilized in the pharmaceutical field can be used.

For example pharmaceutical compositions, usable for the oral administration of the compounds of formula (I) or of the corresponding hydrates or solvates or pharmaceutically acceptable salts, are formed of: 0.5-20% by weight of a compound of formula (I), comprising all the various isomers and the corresponding mixtures or of a corresponding hydrate or solvate or pharmaceutically acceptable salt; 0.05-0.5% by weight of sodium alkylsulphate or of another surfactant; 2.5-10% by weight of a desegregating agent as for example cellulose, sodium carboxymethylcellulose or other cellulose derivatives.

The compounds of formula (I), including the various isomers and related mixtures, and the corresponding hydrates or solvates and pharmaceutically acceptable salts and their pharmaceutical compositions of the present invention have a high affinity in vitro for the cannabinoidergic CB1 and/or CB2 receptors. See the Examples. More specifically the compounds of the present invention have a Ki value for the CB1 and/or CB2 receptors lower than 0.5 µM.

The present invention also relates to the use of compounds of formula (I), including the various isomers and the respective mixtures, the corresponding hydrates or solvates or pharmaceutically acceptable salts, or the pharmaceutical compositions containing them, for preparing products for the treatment in mammalians and in men of diseases wherein the CB1 and/or CB2 receptors are involved.

In particular the compounds of formula (I) comprising the various isomers and respective mixtures, or the corresponding hydrates or solvates or pharmaceutically acceptable salts, or in the form of the corresponding pharmaceutical compositions, having affinity towards the CB2 receptors, can therefore be used in the treatment of diseases in which immune system cells or immune disorders are involved, or in the treatment of other pathologies, as for example osteoporosis, renal ischemia and in case of inflammatory states.

The compounds of the present invention, comprising the various isomers and respective mixtures, and the corresponding hydrates or solvates and pharmaceutically acceptable salts and the respective pharmaceutical compositions, having affinity towards CB2 receptors, can also be used in case of diseases related to organ transplants and preventive rejection therapies in the allogenic transplant, in the transplant rejection treatment also in patients which have received other immunosuppressive therapies, in the treatment and prophylaxis of GVHD (Graft Versus Host Disease), in the treatment of diseases as: erythematous systemic lupus, ankylosing spondylitis, polyarthritis rheumatoid, hemolytic autoimmune anaemia, Behcet disease, Sjögren syndrome, undifferentiated spondylarthritis, reactive arthritis, dermatomyositis.

Furthermore the compounds of formula (I), comprising the various isomers and respective mixtures or the corresponding hydrates or solvates or pharmaceutically acceptable salts, or in the form of the corresponding pharmaceutical compositions, having affinity towards CB1 receptors, can be used in the treatment of ocular diseases, as glaucoma or ocular hypertonia, lung-diseases as asthma and chronic bronchitis, allergies and allergic reactions (for example allergic rhinitis, contact dermatitis, allergic conjunctivitis), inflammations as for example arthritis.

The compounds of formula (I), comprising the various isomers and respective mixtures and the corresponding hydrates or solvates and pharmaceutically acceptable salts and the respective pharmaceutical compositions, having affinity towards CB1 receptors, can also be used as analgesics in the pain treatment, in cases of anxiety, mood problems, delirium states, psychotic afflictions in general, for the schizophrenia, depression treatment, when abuse and/or addiction sub-stances are used (for example alcoholism and tabagism).

The compounds of formula (I) comprising the various isomers and respective mixtures and the corresponding hydrates or solvates and pharmaceutically acceptable salts and the respective pharmaceutical compositions, having affinity towards CB1 receptors, can also be used to contrast vomit, nausea, vertigoes, especially in case of patients subjected to chemotherapy; in the treatment of neuropathies, hemicrania, stress, diseases having a psychosomatic origin, epilepsy, Tourette syndrome, Parkinson disease, Huntington disease, Alzheimer disease, senile dementia, in case of cognitive disease and memory loss, in the treatment of problems connected to appetite (obesity, bulimia), in the treatment of pathologies of the gastrointestinal tract and of the bladder, of cardiovascular diseases, in case of urinary and fertility problems, in the treatment of neuroinflammatory pathologies as for example multiple sclerosis, Guillain-Barré syndrome, viral encephalitis.

Among the compounds object of the present invention, comprising the various isomers and respective mixtures and the corresponding hydrates or solvates and pharmaceutically acceptable salts and their pharmaceutical compositions, those having affinity towards CB1 receptors at least five times, preferably at least ten times higher than that for CB2 receptors, are preferably used for the treatment of diseases wherein the CB1 receptors are involved.

The compounds of formula (I) comprising the isomers and the corresponding mixtures, the corresponding hydrates or solvates or pharmaceutically acceptable salts, or in the form of the corresponding pharmaceutical compositions, having an affinity towards CB2 receptors at least five times, preferably at least ten times higher than that for the CB1 receptors, are instead preferably used for the treatment of diseases wherein the CB2 receptors are involved.

Among the compounds of formula (I) comprising the various isomers and their mixtures, and the corresponding hydrates or solvates and pharmaceutically acceptable salts, and the respective pharmaceutical compositions, those wherein A is formed of —(CH$_2$)$_t$— wherein t=1 are still more preferred for the treatment of pathologies wherein CB2 receptors are involved, when the affinity towards CB2 receptors is at least five times, preferably at least ten times higher than that for CB1 receptors.

The compounds of formula (I) comprising the various isomers and respective mixtures, and the corresponding hydrates or solvates and pharmaceutically acceptable salts, and the respective pharmaceutical compositions, with A —(CH$_2$)$_t$— wherein t=2, 3, are still more preferred for the treatment of diseases wherein CB1 receptors are involved, when the affinity towards CB1 receptors is at least five times, preferably at least ten times higher than that for CB2 receptors.

The use of the compounds of formula (I) comprising the various isomers and respective mixtures, and the corresponding hydrates or solvates and pharmaceutically acceptable salts, and the respective pharmaceutical compositions, for the treatment of the different pathologies wherein the modulation of CB1 and/or CB2 receptors is involved as mentioned above, can be made by utilizing the known methods used for said treatments. In particular the administration of the compounds must be carried out in a sufficiently effective amount for the specific treatment. Analogously the dosages, the administration route and the posology will be established depending on the disease typology, on the pathology seriousness, on the physical conditions and characteristics of the patient (for example age, weight, response to the active principle), on the pharmacokinetics and toxicology of the compounds of formula (I) selected for the specific treatment.

The preferred daily dosage interval is 0.01-100 mg of compound of formula (I) of the invention per Kg of body weight of mammalian to be treated. In men, the preferred daily dosage interval is 0.1-1000 mg of compound per Kg of body weight, still more preferred from 1 to 200 mg.

A further object of the present invention is the use of compounds of formula (I) comprising the isomers and the corresponding mixtures, or of the corresponding hydrates or solvates or pharmaceutically acceptable salts, radiomarked, and of the respective pharmaceutical formulations, for the identification and the marking of the cannabinoidergic CB1 or CB2 receptors in mammalians or in men.

The following Examples are given to better understand the present invention and are not anyway limitative.

EXAMPLES

Example 1.1

Preparation of the Ethyl Ester of the 7-chloro-1-(2', 4'-dichlorophenyl)-4,5-dihydro-1H-thieno[2,3-g] indazol-3-carboxylic Acid

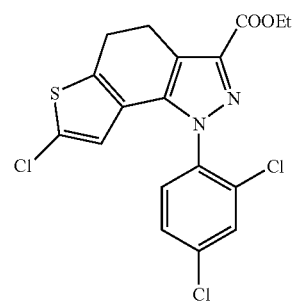

1.1.0 Preparation of the Compound 2-chloro-4,5,6,7-tetrahydro-benzo[b]thiophene-4-one To a solution of 4,5,6,7-tetrahydro-benzo[b]thiophen-4-one (0.5 g, 3.28 mmoles) [Tanaka H. Et Al. Eur. J. Med. Chem. 1997 32 607-615] in glacial acetic acid (5 ml), N-chlorosuccinimide (0.53 g, 8.93 mmoles) was added and the reaction mixture was kept under reflux under stirring for 1 hour. Then the solvent was removed under reduced pressure. The residue is treated with a $NaHCO_3$ aqueous solution at 10% and it is extracted with ethyl acetate. The organic phase is washed with water and dried over $Na_2SO_4$. It is concentrated under reduced pressure obtaining an oil which is purified by flash chromatography (oil ether/ethyl acetate 9/1 on silica gel). 0.36 g (60% yield) of the compound are recovered under the form of a yellow oil. Rf=0.67 (oil ether/ethyl acetate 9/1 on silica gel); m.p.: 95° C.;

IR (film) ($\lambda=cm^{-1}$) 1700 (C=O); $^1$H-NMR ($CDCl_3$) δ 2.10-2.23 (m 2H); 2.49 (t, 2H, J=6.0 Hz) 2.89 (t, 2H, J=6.0 Hz); 7.13 (s, 1H);

Anal. calc. for $C_{12}H_{11}ClO_4S$: C, 51.48; H, 3.78; Cl, 18.99; S, 17.18. Found: C, 51.13; H, 3.44; Cl, 19.23; S, 17.23.

1.1a Preparation of the Compound Ethyl 2-chloro-4-oxy-4,5,6,7-tetrahydro-1-benzo[b]thiophene-5-carboxylate Metal sodium (0.22 g; 9.42 mmol) was added in small pieces to absolute ethanol (5 ml) leaving it under reflux until complete solubilization. To the so obtained mixture diethyloxalate (0.70 g; 0.65 ml; 4.7 mmol) was added, then dropwise a solution of 2-chloro-4,5,6,7-tetrahydro-benzo[b]thiophen-4-one (0.88 g; 4.7 mmol) in absolute ethanol (4-5 ml). The reaction mixture is kept under stirring at room temperature for 1 hour and then poured in ice and HCl 1N. An yellow precipitate is obtained which is filtered under vacuum, washed in water and dried in stove. 1.31 g (97% yield) of the compound 1.1a (compound (IV) in the above reported synthesis scheme) are recovered, which results to be analytically pure. Rf=0.67 (oil ether/ethyl acetate 8/2 on silica gel); m.p.: 95° C.;

IR (nujol) ($\lambda=cm^{-1}$) 3440 (OH as tautomer mixture), 1725 (COOEt), 1680 (C=O); $^1$H-NMR ($CDCl_3$) δ 1.37-1.44 (t, 3H, J=7.0 Hz); 2.90-2.97 (t, 2H, J=7.0 Hz); 3.12-3.19 (t, 2H, J=7.0 Hz); 4.35-4.42 (q, 2H, J=7.0 Hz); 7.23 (s, 1H);

Anal. calc. for $C_{12}H_{11}ClO_4S$: C, 50.27; H, 3.87; Cl, 12.36; S, 11.18. Found: C, 49.99; H, 4.03; Cl, 12.48; S, 11.24.

1.1b Preparation of the Compound Ethyl Ester of the 7-chloro-1-(2',4'-dichlorophenyl)-4,5-dihydro-1H-thieno[2,3-g] indazol-3-carboxylic Acid A mixture is prepared consisting of the compound prepared in 1.1a (0.5 g; 175 mmol) and 2,4-dichlorophenylhydrazine hydrochloride (0.41 g; 1.93 mmol) in ethanol (11.67 ml). The mixture is reacted at the reflux temperature for 2 hours, then cooled down to room temperature. After the solvent removal, a reddish solid is obtained. The raw solid was treated with oil ether and purified by flash chromatography (oil ether/ethyl acetate 9/1 on silica gel), obtaining 0.5 g (67% yield) of the ester 1.1b under the form of a light-coloured solid. Rf=0.3 (oil ether/ethyl acetate 9/1 on silica gel); m.p.: 144° C.;

IR (nujol) ($\lambda=cm^{-1}$) 3440 (OH as tautomer mixture), 1725 (COOEt), 1603 (C=O); $^1$H-NMR ($CDCl_3$) δ 1.38-1.45 (t, 3H, J=7.0 Hz); 2.90-3.0 (t, 2H, J=10.0 Hz); 3.22-3.32 (t, 2H, J=10.0 Hz); 4.4-4.5 (q, 2H, J=7.0 Hz); 5.99 (s, 1H); 7.44-7.46 (d, 2H); 7.60 (s, 1H);

Anal. calc. for $C_{18}H_{13}Cl_3N_2O_2S$: C, 50.54; H, 3.06; Cl, 24.87; N, 6.55; S, 7.50. Found: C, 50.58; H, 2.88; Cl, 25.06; N, 6.78; S, 7.13.

Example 1.2

Preparation of the Ethyl Ester of the 7-bromo-1-(2',4'-dichlorophenyl)-4,5-dihydro-1H-thieno[2,3-g] indazol-3-carboxylic Acid The same procedure described in 1.1b is followed but reacting with 2,4-dichlorophenylhydrazine the compound ester ethyl 2-bromo-7-oxy-4,5,6,7-tetrahydro-1-benzo[b]thiophene-6-carboxylate, obtained starting from 2-bromo-4,5,6,7-tetrahydro-1-benzo[b]thiophene-4-one according to the process described in Pinna G. A. et Al. Eur. J. Med. Chem. 1994 29 447-454. The obtained raw solid was purified by flash chromatography (oil ether/ethyl acetate 9/1), obtaining the expected compound under the form of a white solid (73% yield). Rf=0.4 (oil ether/ethyl acetate 9/1); m.p.: 95-97° C.;

IR (nujol) ($\lambda=cm^{-1}$) 1726 (COOEt), 1610 (C=O); $^1$H-NMR ($CDCl_3$) δ 1.38-1.46 (t, 3H, J=8.0 Hz); 2.98-3.06 (t, 2H, J=8.0 Hz); 3.20-3.28 (t, 2H, J=8.0 Hz); 4.4-4.6 (q, 2H, J=8.0 Hz); 6.12 (s, 1H); 7.45-7.46 (d, 2H); 7.61 (s, 1H);

Anal. calc. for $C_{18}H_{13}BrCl_2N_2O_2S$: C, 45.79; H, 2.78; Br, 16.92; Cl, 15.02; N, 5.93; S, 6.79. Found: C, 45.67; H, 2.92; Br, 17.03; Cl, 14.89; N, 6.03; S, 6.82.

Example 1.3

Preparation of the Ethyl Ester of the 1-(5'-chloro pentyl)-4,5-dihydro-1H-thieno[3,2-g]indazol-3-carboxylic Acid A solution of ethyl 7-oxy-4,5,6,7-tetrahydro-1-benzo[b]thiophene-6-carboxylate (0.88 g, 3.52 mmol), obtained starting from 4,5,6,7-tetrahydro-1-benzo[b]thiophene-7-one as described in Pinna G. A. et al. J. Chem. Res., 1993, 1273-1281, and of 5-chloropentylhydrazine hydrochloride (0.67 g, 3.87 mmol) in 24 ml of EtOH was refluxed for 24 hours. The obtained raw solid, after the solvent was removed, was purified by flash chromatography (oil ether/ethyl acetate 8/2), obtaining the corresponding tricyclic ester derivative under the form of a white solid (64% yield). Rf=0.194 (oil ether/ethyl acetate 8/2); m.p.: 62-64° C.;

IR (nujol) ($\lambda=cm^{-1}$) 1715 (COOEt); 1H-NMR ($CDCl_3$) δ 1.42 (t, 3H, J=7.8 Hz); 1.50-1.65 (m, 2H); 1.76-2.08 (m, 4H); 2.93 (t, 2H, J=7.4 Hz); 3.10 (t, 2H, J=7.4 Hz); 3.53 (t, 2H, J=6.6 Hz); 4.33-4.47 (m, 4H); 7.01 (d, 1H, J=4.6 Hz); 7.27 (d, 1H, J=3.6 Hz);

Anal. calc. for $C_{17}H_{21}ClN_2O_2S$: C, 57.86; H, 6.00; Cl, 10.05; N, 7.94; S, 9.09. Found: C, 57.67; H, 5.92; Cl, 9.89; N, 7.93; S, 9.02.

Example 1.4

Synthesis of the Ethyl Ester of the 7-chloro-1-(5'-chloro pentyl)-4,5-dihydro-1H-thieno[3,2-g] indazol-3-carboxylic Acid

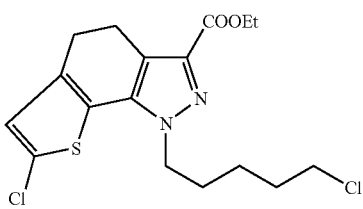

A solution of the compound obtained in 1.3 (0.71 g, 2.01 mmol) and of N-chlorosuccinimide (0.32 g, 2.42 mmol) in 6.31 ml of AcOH is refluxed for 2 hours. After cooling to room temperature, a 10% NaHCO3 aqueous solution is cautiously added. The organic phase is extracted with $CH_2Cl_2$, anhydrified over $Na_2SO_4$ and concentrated by evaporating the solvent. An oily, product is obtained which is treated with oil ether. It is filtered and the solid is dried in the air. The expected compound appears as a cream-coloured solid (70.5% yield). Rf=0.375 (oil ether/ethyl acetate 8/2); m.p.: 58-60° C.;

IR (nujol) ($\lambda$=cm$^{-1}$) 1722 (COOEt); 1H-NMR (CDCl$_3$) $\delta$ 1.41 (t, 3H, J=7.2 Hz); 1.48-1.65 (m, 2H); 1.72-2.08 (m, 4H); 2.84 (t, 2H, J=8.0 Hz); 3.08 (t, 2H, J=8.0 Hz); 3.53 (t, 2H, J=6.6 Hz); 4.28 (t, 2H, J=7.8 Hz); 4.41 (q, 2H, J=7.2 Hz); 6.85 (s, 1H);

Anal. calc. for $C_{17}H_{20}Cl_2N_2O_2S$: C, 52.72; H, 5.20; Cl, 18.30; N, 7.23; S, 8.27. Found: C, 52.63; H, 5.15; Cl, 18.22; N, 7.19; S, 8.25.

Examples of other compounds of formula (VI), obtained according to the general procedures of the Examples 1.1-1.4, prepared starting from known compounds of the prior art, are reported in Table 1. In the Table for each synthesized compound are indicated: reaction yield by percentage (% yield), the melting point in degrees centigrade (m.p. ° C.), the empirical formula, the wave length of the IR band corresponding to the group —COOEt ($\lambda$), the significant peaks of the $^1$H-NMR analysis in CDCl$_3$ ($^1$H-NMR $\delta$ ppm).

In the Tables E, G and F indicate the ring atom and the group formed by the atom linked to the corresponding substituent.

TABLE 1 (VI)

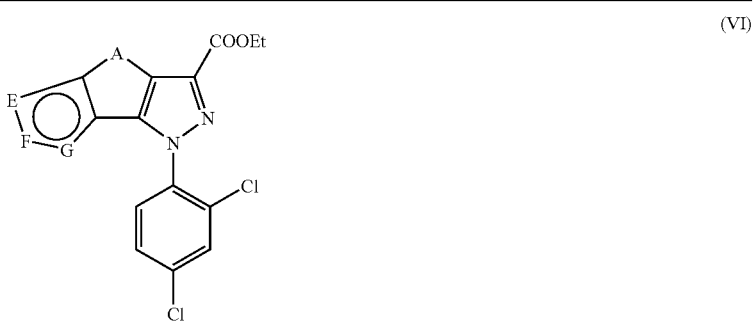

| EX. | E | F | G | A | Yield % | m.p.: ° C. | Empirical Formula | IR ($\lambda$ = cm$^{-1}$) | $^1$H-NMR $\delta$ ppm |
|---|---|---|---|---|---|---|---|---|---|
| 1.5 | S | C—CH$_3$ | CH | CH$_2$—CH$_2$ | 72 | 150-151 | $C_{19}H_{16}Cl_2N_2O_2S$ | 1713 (COOEt) | 1.41(t, 3 H, J = 7.0 Hz); 2.31(s, CH$_3$): 3.01(t, 2 H, J = 9.0 Hz); 3.21(t, 2 H, J = 9.0 Hz); 4.42(q, 2 H, J = 7.0 Hz); 5.83(s, 1 H); 7.44(d, 2 H); 7.50(s, 1 H); |
| 1.6 | C—Br | CH | S | CH$_2$—CH$_2$ | 93 | 177-179 | $C_{18}H_{13}BrCl_2N_2O_2S$ | 1732 (COOEt) | 1.43(t, 3 H, J = 7.0 Hz); 2.96(t, 2 H, J = 8.0 Hz); 3.22(t, 2 H, J = 8.0 Hz); 4.45(q, 2 H, J = 7.0 Hz); 7.07(s, 1 H); 7.46-7.47(m, 2 H); 7.60(s, 1 H); |
| 1.7 | CH | C—Cl | S | CH$_2$—CH$_2$ | 59 | 171 | $C_{18}H_{13}Cl_3N_2O_2S$ | 1715 (COOEt) | 1.43(t, 3 H, J = 7.0 Hz); 2.95(t, 2 H, J = 10.0 Hz); 3.28(t, 2 H, J = 10.0 Hz); 4.45(q, 2 H, J = 7.0 Hz); 5.99(s, 1 H); 7.44-7.46(d, 2 H); 7.80(s, 1 H); |
| 1.8 | S | C—Cl | CH | CH$_2$—CH$_2$—CH$_2$ | 89 | 169 | $C_{19}H_{15}Cl_3N_2O_2S$ | 1709 (COOEt), | 1.4(t, 3 H, J = 7.0 Hz); 1.88-2.00(m, 4 H); 2.74(t, 2 H, J = 5.6 Hz); 4.37(q, 2 H, J = 7.0 Hz); 6.50(s, 1 H); 7.15-7.31(m, 3 H); |
| 1.9 | S | C—Br | CH | CH$_2$—CH$_2$—CH$_2$ | 78 | 160-162 | $C_{19}H_{15}BrCl_2N_2O_2S$ | 1724 (COOEt), | 1.42(t, 3 H, J = 7.0 Hz); 1.86-2.00(m, 4 H); 2.75(t, 2 H, J = 5.4 Hz); 4.36(q, 2 H, J = 7.0 Hz); 6.70(s, 1 H); 7.13-7.28(m, 3 H); |
| 1.10 | CH | C—Cl | S | CH$_2$—CH$_2$—CH$_2$ | 71 | 158 | $C_{19}H_{15}Cl_3N_2O_2S$ | 1715 (COOEt), | 1.42(t, 3 H, J = 7.0 Hz); 1.88-2.06(m, 4 H); 2.73-2.78 (m, 2 H); 4.35(q, 2 H, J = 7.0 Hz); 6.83(s, 1 H); 7.18-7.33(m, 3 H); |
| 1.11 | CH | C—Br | S | CH$_2$—CH$_2$—CH$_2$ | 82 | 166 | $C_{19}H_{15}BrCl_2N_2O_2S$ | 1726 (COOEt), | 1.38(t, 3 H, J = 7.0 Hz); 1.86-2.08(m, 4 H); 2.75-2.82 (m, 2 H); 4.38(q, 2 H, J = 7.0 Hz); 7.00(s, 1 H); 7.23-7.37(m, 3 H); |

TABLE 1-continued

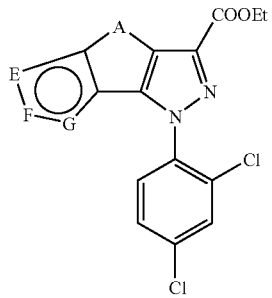

(VI)

| EX. | E | F | G | A | Yield % | m.p.: °C. | Empirical Formula | IR (λ = cm$^{-1}$) | $^1$H-NMR δ ppm |
|---|---|---|---|---|---|---|---|---|---|
| 1.12 | S | CH | CH | CH2—CH2—CH2 | 48 | 157-159 | C$_{19}$H$_{16}$Cl$_2$N$_2$O$_2$S | 1713 (COOEt) | 1.42(t, 3 H, J = 7.0 Hz); 2.10-2.20(m, 2 H); 3.02(t, 2 H, J = 5.4 Hz); 3.18-3.30(m, 2 H); 4.44(q, 2 H, J = 7.0 Hz); 6.17(d, 1 H, J = 6.0 Hz); 6.84(d, 1 H, J = 6.0 Hz); 7.40(d, 1 H, J = 2.0 Hz); 7.44(s, 1 H); 7.51(d, 1 H, J = 1.8 Hz); |
| 1.13 | S | C—CH$_3$ | CH | CH$_2$ | 78 | 142 | C$_{18}$H$_{14}$Cl$_2$N$_2$O$_2$S | 1712 (COOEt), | 1.42(t, 3 H, J = 7.0 Hz); 2.31(t, CH$_3$); 3.71(s, 2 H); 4.44(q, 2 H, J = 7.0 Hz); 5.83(s, 1 H); 7.42-7.44(m, 2 H); 7.50(s, 1 H); |
| 1.14 | CH | C—CH$_3$ | S | CH$_2$ | 69 | 152 | C$_{18}$H$_{14}$Cl$_2$N$_2$O$_2$S | 1722 (COOEt), | 1.39(t, 3 H, J = 7.0 Hz); 2.27(s, CH$_3$); 3.81(s, 2 H); 4.44(q, 2 H, J = 7.0 Hz); 5.70(s, 1 H); 7.40-7.44(d, 2 H); 7.49(s, 1 H) |

Example 2.1

Preparation of the 7-chloro-1-(2',4'-dichlorophenyl)-4,5-dihydro-1H-thieno[2,3-g] indazol-3-carboxylic Acid To a solution formed by the ester obtained in 1.1 (0.49 g; 1.14 mmol) in methanol (10 ml), KOH (0.130 g; 2.28 mmol) solubilized in methanol (4-2 ml) was added. The reaction mixture was kept under stirring at the reflux temperature for 8 hours. At the end it was poured in water and ice and acidified with HCl 1N. The precipitate was filtered under vacuum, washed with H$_2$O and dried in a stove obtaining 0.40 g (89% yield) of the corresponding acid in the form of an analytically pure white solid. Rf=0.41 (chloroform/methanol 9/1); m.p.: 247° C.;

IR (nujol) (λ=cm$^{-1}$) 3410 (OH), 1678 (C=); $^1$H-NMR (CDCl$_3$) δ 2.97-3.04 (t, 2H, J=7.0 Hz); 3.21-3.28 (t, 2H, J=7.0 Hz); 6.0 (s, 1H); 7.34 (s, 1H, OH exchanges with D$_2$O); 7.46-7.47 (d, 2H); 7.61 (s, 1H);

Anal. calc. for C$_{16}$H$_9$Cl$_3$N$_2$O$_2$S: C, 48.08; H, 2.27; Cl, 26.61; N, 7.01; S, 8.02. Found: C, 48.44; H, 1.99; Cl, 26.28; N, 6.86; S, 7.98.

Example 2.2

Preparation of the 7-bromo-1-(2',4'-dichlorophenyl)-4,5-dihydro-1H-thieno[2,3-g] indazol-3-carboxylic Acid The same procedure described in the Example 2.1 was followed to convert the ethyl ester obtained in the Example 1.2 into the corresponding acid. The yield is 98%; Rf: 0.37 (chloroform/methanol 9/1); m.p.: 235-237° C.;

IR (nujol) (λ=cm$^{-1}$) 3408 (OH), 1682 (C=O); $^1$H-NMR (CDCl$_3$) δ 2.98-3.03 (t, 2H, J=5.0 Hz); 3.22-3.27 (t, 2H, J=5.0 Hz); 6.13 (s, 1H); 7.47 (s, 2H); 7.63 (s, 1H);

Anal. calc. for C$_{16}$H$_9$BrCl$_2$N$_2$O$_2$S: C, 43.27; H, 2.04; Br, 17.99; Cl, 15.96; N, 6.31; S, 7.22. Found: C, 43.33; H, 1.98; Br, 18.15; Cl, 16.22; N, 6.56; S, 6.98.

Example 2.3

Preparation of the 7-chloro-1-(5'-chloropentyl)-4,5-dihydro-1H-thieno[3,2-g] indazol-3-carboxylic Acid The same procedure described in the Example 2.1 is utilized to convert the ester prepared in the Example 1.4 into the corresponding acid. The yield is 94%. Rf=0.35 (chloroform/methanol 95/5); m.p.: 205-208° C.;

IR (nujol) (λ=cm$^{-1}$) 1688 (COOH); 1H-NMR (CDCl$_3$) δ 1.48-1.65 (m, 2H); 1.75-2.10 (m, 4H); 2.84 (t, 2H, J=7.6 Hz); 3.08 (t, 2H, J=7.6 Hz); 3.54 (t, 2H, J=6.6 Hz); 4.28 (t, 2H, J=8.2 Hz); 4.41 (q, 2H, J=7.2 Hz); 6.87 (s, 1H); Anal. calc. For C$_{15}$H$_{16}$Cl$_2$N$_2$O$_2$S: C, 50.15; H, 4.49; Cl, 19.73; N, 7.79; S, 8.92.

Found: C, 50.08; H, 4.43; Cl, 19.70; N, 7.72; S, 8.90.

Examples of other compounds of formula (II), obtained by using the above described processes, are reported in Table 2. The acid 2.4 of Table 2 was obtained from the ester of the Example 1.5 of Table 1; the acid 2.5 was obtained from the ester of the Example 1.6, and so on.

TABLE 2

(II)

[Structure: fused ring system with A, E, F, G labels, COOH group, and 2,4-dichlorophenyl substituent]

| Ex. | E | F | G | A | Yield % | m.p.: °C | Empirical Formula | IR (λ = cm⁻¹) | ¹H-NMR δ ppm |
|---|---|---|---|---|---|---|---|---|---|
| 2.4 | S | C—CH₃ | CH | CH₂—CH₂ | 90 | 258 | C₁₇H₁₂Cl₂N₂O₂S | 3409 (OH), 1697 (C=O); | 2.32(s, CH₃); 3.01-3.05(m, 2 H); 3.16-3.20(m, 2 H); 3.78(br s, 1 H, OH exch. with D₂O); 5.83(s, 1 H); 7.50(s, 2 H); 7.65(s, 1 H) |
| 2.5 | C—Br | CH | S | CH₂—CH₂ | 89 | 239-242 | C₁₆H₉BrCl₂N₂O₂S | 3413 (OH), 1694 (C=O); | 2.97(t, 3 H, J = 8.0 Hz); 3.24(t, 2 H, J = 8.0 Hz); 5.86(br s, 1 H, OH exch. with D₂O); 7.09(s, 1 H); 7.44-7.46(m, 2 H); 7.62(s, 1 H); |
| 2.6 | CH | C—Cl | S | CH₂—CH₂ | 89 | 252-254 | C₁₆H₉Cl₃N₂O₂S | 3410 (OH), 1690 (C=O); | 2.95(t, 3 H, J = 8.0 Hz); 3.26(t, 2 H, J = 8.0 Hz); 5.90(br s, 1 H, OH exch. with D₂O); 6.90(s, 1 H); 7.44-7.46(m, 2 H); 7.63(s, 1 H); |
| 2.7 | S | C—Br | CH | CH₂—CH₂—CH₂ | 79 | 247 | C₁₆H₉BrCl₂N₂O₂S | 3419 (OH), 1720 (C=O); | 1.86-2.00(m, 4 H); 2.71-2.76(m, 2 H); 3.44(br s, 1 H, OH exch. with D₂O); 6.70(s, 1 H); 7.13-7.28(m, 3 H); |
| 2.8 | S | C—Cl | CH | CH₂—CH₂—CH₂ | 69 | 255 | C₁₆H₉Cl₃N₂O₂S | 3419 (OH), 1716 (C=O); | 1.88-2.06(m, 4 H); 2.74-2.80(m, 2 H); 3.51(br s, 1 H, OH exch. with D₂O); 6.55(s, 1 H); 7.15-7.31(m, 3 H); |
| 2.9 | CH | C—Br | S | CH₂—CH₂—CH₂ | 71 | 261 | C₁₆H₉BrCl₂N₂O₂S | 3470 (OH), 1692 (C=O); | 1.88-2.04(m, 4 H); 2.68-2.77(m, 2 H); 3.41(br s, 1 H, OH exch. with D₂O); 6.92(s, 1 H); 7.14-7.32(m, 3 H); |
| 2.10 | CH | C—Cl | S | CH₂—CH₂—CH₂ | 90 | 254-257 | C₁₆H₉Cl₃N₂O₂S | 3377 (OH), 1682 (C=O); | 1.88-2.06(m, 4 H); 2.74-2.80(t, 2 H); 3.51(br s, 1 H, OH exch. with D₂O); 6.85(s, 1 H); 7.21-7.35(m, 3 H); |
| 2.11 | S | CH | CH | CH₂—CH₂—CH₂ | 92 | 218-220 | C₁₇H₁₂Cl₂N₂O₂S | 1687 (C=O); | 2.05-2.20(m, 2 H); 3.02(t, 2 H, J = 5.8 Hz); 3.20-3.30(m, 2 H); 6.18(d, 1 H, J = 6.0 Hz); 6.85(d, 1 H, J = 6.0 Hz); 7.37-7.51(m, 3 H); 12.70(br s, 1 H, OH exch. with D₂O); |
| 2.12 | S | C—CH₃ | CH | CH₂ | 89 | 63 | C₁₆H₁₀Cl₂N₂O₂S | 3470 (OH), 1692 (C=O); | 2.41(s, CH₃); 3.81(s, 2 H); 3.78(br s, 1 H, OH exch. with D₂O); 6.40(s, 1 H); 7.35(s, 2 H); 7.58(s, 1 H) |
| 2.13 | CH | C—CH₃ | S | CH₂ | 92 | 248 | C₁₆H₁₀Cl₂N₂O₂S | 3377 (OH), 1682 (C=O); | 2.38(s, CH₃); 3.79(s, 2 H); 3.95(br s, 1 H, OH exch. with D₂O); 6.51(s, 1 H); 7.42(s, 2 H); 7.62(s, 1 H) |

Example 3.1

Preparation of N-piperidinyl-7-chloro-1-(2',4'-dichloro phenyl)-4,5-dihydro-1H-thieno[2,3-g]indazol-3-carboxamide 3.1a Preparation of the Chloride of the 7-chloro-1-(2',4'-dichlorophenyl)-4,5-dihydro-1H-thieno[2,3-g] indazol-3-carboxylic Acid To a solution formed by the acid obtained in the Example 2.1 (0.34 g; 0.85 mmol) in toluene (7 ml), SOCl₂ (0.303 g; 0.2 ml; 2.55 mmol) was added. The mixture was kept under stirring at the reflux temperature for 2 hours and 30 min. At the end the solvent was removed and the obtained solid residue was treated twice with fresh toluene bringing then each time to dryness. 0.36 g (100% yield) of compound were recovered.

3.1b Preparation of N-piperidinyl-7-chloro-1-(21,41-dichlorophenyl)-4,5-dihydro-1H-thieno[2,3-g]indazol-3-carboxamide A solution in CH₂Cl₂ (3-4 ml) of the previous compound (0.36 g; 0.88 mmol) was added to a solution of 1-aminopiperidine (0.14 ml; 0.13 g; 1.33 mmol) and TEA (0.19 ml; 1.33 mmol) in CH₂Cl₂ (3-4 ml) cooled in an ice bath. The reaction mixture was kept under stirring at room temperature overnight. Then it was diluted with salt H₂O, extracted with CH₂Cl₂ and washed with salt H₂. The organic phases were joined, dehydrated with anhydrous sodium sulphate and concentrated under vacuum. After the solvent was removed, the obtained residue was treated with oil ether and purified by flash chromatography (oil ether/ethyl acetate 6/4) obtaining 0.13 g (32% yield) of compound under the form of a white solid. Rf=0.4 (oil ether/ethyl acetate 6/4); m.p.: 150° C.;

IR (nujol) ($\lambda$=cm$^{-1}$) 3200 (NH), 1650 (C=O); $^1$H-NMR (CDCl$_3$) $\delta$ 1.42-1.44 (m, 2H); 1.72-1.77 (m, 4H); 2.82-2.87 (t, 4H); 2.95-3.03 (t, 2H, J=8.0 Hz); 3.26-3.34 (t, 2H, J=8.0 Hz); 5.98 (s, 1H); 7.45 (s, 2H); 7.58 (br s, 1, NH exchanges with D$_2$O); 7.64 (s, 1H); $^{13}$C-NMR (CDCl$_3$) $\delta$ 19.97 (CH$_2$); 23.29 (CH$_2$); 24.10 (CH$_2$); 25.36 (2×CH$_2$); 57.11 (2×CH$_2$); 116.99 (C); 119.631 (CH); 124.93 (C); 128.05 (C); 128.28 (CH); 130.35 (CH); 130.54 (CH); 133.42 (C); 135.78 (C); 136.81 (C); 138.02 (C); 138.61 (C); 142.72 (C); 159.60 (CO); Anal. calc. for C$_{21}$H$_{19}$Cl$_3$N$_4$OS: C, 52.35; H, 3.97; Cl, 22.07; N, 11.63; S, 6.66. Found; C, 52.12; H, 4.12; Cl, 21.99; N, 11.45; S, 6.58.

Example 3.2

Preparation of N-piperidinyl-7-bromo-1-(2',4'-dichloro phenyl)-4,5-dihydro-1H-thieno[2,3-g]indazol-3-carboxamide The same procedure described in the preparations a) and b) of Example 3.1. was used to react the 7-bromo-1-(2',4'-dichlorophenyl)-4,5-dihydro-1H-thieno[2,3-g] indazol-3-carboxylic acid prepared in the Example 2.2 with 1-aminopiperidine. The purification by flash chromatography (oil ether/ethyl acetate 6/4) has given the compound N-piperidinyl-7-bromo-1-(2',4'-dichlorophenyl)-4,5-dihydro-1H-thieno[2,3-g]indazol-3-carboxamide as white solid with a 42% yield. Rf=0.33 (oil ether/ethyl acetate 6/4); m.p.: 145° C.;

IR (nujol) ($\lambda$=cm$^{-1}$) 3202 (NH), 1605 (C=O); $^1$H-NMR (CDCl$_3$) $\delta$ 1.42-1.43 (m, 2H) 1.72-1.74 (m, 4H); 2.82-2.87 (m, 4H); 2.95-3.03 (t, 2H, J=8.0 Hz); 3.25-3.33 (t, 2H, J=8.0 Hz); 6.11 (s, 1H); 7.45 (s, 2H); 7.60 (br s, 1H, NH exchanges with D$_2$O); 7.63 (s, 1H); $^{13}$C-NMR (CDCl$_3$) $\delta$ 19.99 (CH$_2$); 23.26 (CH$_2$); 24.25 (CH$_2$); 25.33 (2×CH$_2$); 57.05 (2×CH$_2$); 110.12 (C); 116.96 (C); 123.17 (C); 126.08 (C); 128.28 (CH); 130.31 (CH); 130.52 (CH); 133.36 (C); 135.74 (C); 136.78 (C); 138.51 (C); 140.95 (C); 142.62 (C); 159.52 (CO); Anal. calc. for C$_{21}$H$_{19}$BrCl$_2$N$_4$OS: C, 47.93; H, 3.64; Br, 15.18; Cl, 13.10; N, 10.65; S, 6.09.

Found: C, 48.15; H, 3.36; Br, 14.99; Cl, 13.12; N, 10.82; S, 5.98.

Example 3.3

Preparation of N-pentyl-7-chloro-1-(2',4'-dichlorophenyl)-4,5-dihydro-1H-thieno[3,2-g]indazol-3-carboxamide 3.3a Preparation of a Reactive Derivative (Adduct) of the -7-chloro-1-(2',4'-dichlorophenyl)-4,5-dihydro-1H-thieno[3,2-g]indazol-3-carboxylic Acid To a suspension of the acid prepared in the Example 2.1 (0.5 g, 1.25 mmol) in 6 ml of CH$_2$Cl$_2$, 1-hydroxybenzotriazole (0.20 g, 1.47 mmol) and EDC (1-(3-diamino propyl)-3-ethylcarbodiimide hydrochloride (0.28 g, 1.47 mmol), were added. When the solution became homogeneous, 10 main elapsed, the solution was used as such for the subsequent step without isolating the amide which has formed.

3.3b Preparation of N-pentyl-7-chloro-1-(2',4'-dichlorophenyl)-4,5-dihydro-1H-thieno[3,2-g]indazol-3-carboxamide To the homogeneous solution obtained in 3.3a an additional solution was added obtained by dissolving 1-pentylamine (0.16 g, 1.87 mmol) in 4.2 ml of CH$_2$Cl$_2$. The mixture is kept under stirring for 7 hours. At the end the solvent was removed. The residue which was isolated was purified by flash chromatography (oil ether/ethyl acetate 9/1) obtaining the compound N-pentyl-7-chloro-1-(2',4'-dichlorophenyl)-4,5-dihydro-1H-thieno[2,3-g]indazol-3-carboxamide under the form of a yellow oil (26% yield). Rf=0.10 (oil ether/ethyl acetate 9/1); IR (nujol) ($\lambda$=cm$^{-1}$) 3333 (NH), 1680 (C=O); $^1$H-NMR (CDCl$_3$) $\delta$ 0.68-0.85 (m, 3H); 1.13-1.35 (m, 4H); 1.40-1.58 (m, 2H); 2.77 (t, 2H, J=8.0 Hz); 3.09-3.29 (m, 4H); 6.64 (s, 1H); 6.79 (t, 1H, NH exchanges with D$_2$O); 7.28-7.40 (m, 2H); 7.51 (s, 1H); $^{13}$C-NMR (CDCl$_3$) $\delta$ 13.94 (CH$_3$); 19.65 (CH$_2$); 22.32 (CH$_2$); 24.93 (CH$_2$); 29.07 (CH$_2$); 29.32 (CH$_2$); 38.98 (CH$_2$); 116.49 (C); 121.30 (C); 126.77 (CH); 128.30 (CH); 129.75 (C); 130.64 (2×CH); 133.98 (C); 134.64 (C); 137.25 (C); 138.52 (C); 138.61 (C); 143.58 (C); 162.16 (CO); Anal. calc. for C$_{21}$H$_{20}$Cl$_3$N$_3$OS: C, 53.80; H, 4.30; Cl, 22.69; N, 8.96, S, 6.84.

Found: C, 53.85; H, 4.33; Cl, 22.74; N, 8.99; S, 6.89.

Example 3.4

Preparation of N-myrtanyl-7-chloro-1-(5'-chloropentyl)-4,5-dihydro-1H-thieno[3,2-g]indazol-3-carboxamide The same procedure illustrated in the Example 3.3 is used by reacting the acid obtained in the Example 2.3 (0.2 g, 0.56 mmol) with a solution of myrtanylamine (0.14 ml, 0.84 mmol) in 2 ml of CH$_2$Cl$_2$, by reacting under stirring for 30 min at room temperature. The obtained residue was purified by flash chromatography (oil ether/ethyl acetate 85/15), isolating the compound N-myrtanyl-7-chloro-1-(5'-chloropentyl) 4,5-dihydro-1H-thieno[2,3-g]indazol-3-carboxamide under the form of a yellow oil (56% yield). Rf=0.275 (oil ether/ethyl acetate 85/15);

IR (nujol) ($\lambda$=cm$^{-1}$) 3320 (NH), 1670 (C=O); $^1$H-NMR (CDCl$_3$) $\delta$ 1.08 (s, 3H); 1.21 (s, 3H); 1.50-1.65 (m, 4H); 1.78-2.05 (m, 9H); 2.30-2.42 (m, 2H); 2.81 (t, 2H, J=8.4 Hz); 3.14 (t, 2H, J=8.4 Hz); 3.28-3.48 (m, 2H); 3.55 (t, 2H, J=7.4 Hz); 4.19 (t, 2H, J=7.6 Hz); 6.84 (s, 1H); 6.90 (br s, 1H, NH exchanges with D$_2$O); $^{13}$C-NMR (CDCl$_3$) $\delta$ 19.66 (CH$_2$); 19.80 (CH$_2$); 23.19 (CH$_3$); 23.82 (CH$_2$); 25.06 (CH$_2$); 25.97 (CH$_2$); 27.94 (CH$_3$); 29.42 (CH$_2$); 31.85 (CH$_2$); 33.23 (CH$_2$); 41.29 (CH); 41.46 (CH); 43.82 (CH); 44.45 (CH$_2$); 44.54 (CH$_2$); 50.65 (CH$_2$); 116.86 (C); 121.80 (C); 127.18 (CH); 128.57 (C); 136.03 (C); 138.10 (C); 141.14 (C); 162.56 (CO); Anal. calc. for C$_{25}$H$_{33}$Cl$_2$N$_3$OS: C, 60.72; H, 6.73; Cl, 14.34; N, 8.50; S, 6.48. Found: C, 60.77; H, 6.71; Cl, 14.31; N, 8.48; S, 6.43.

Examples of other compounds of formula (I), obtained according to the general procedures of the Examples 3.1-3.4 prepared starting from the compounds 2.1-2.13 and from similar compounds of formula (II), are described in Table 3.

For example, the acid synthesized in the Example 2.4 of Table 2 was used to obtain the amide according to the Example 3.10 in Table 3. The acid prepared in the Example 2.5 was used to obtain the amide of the Example 3.13; the acid of the Example 2.6 for the amide of the Example 3.12; the acid of the Example 2.7 for the amide of the Example 3.16; the acid of the Example 2.8 for the amide of the Example 3.15; the acid of the Example 2.9 for the amide of the Example 3.18; the acid of the Example 2.10 for the amide of the Example 3.17; the acid of the Example 2.11 for the amide of the Example 3.19; the acid of the Example 2.12 for the amide of the Example 3.20; the acid of the Example 2.13 for the amide of the Example 3.21;

TABLE 3

(I)

| Ex. | E | F | G | A | T' | Yield % |
|---|---|---|---|---|---|---|
| 3.5 | S | C—Cl | CH | CH$_2$—CH$_2$ | pyrrolidinyl | 33 |
| 3.6 | S | C—Cl | CH | CH$_2$—CH$_2$ | azepanyl | 35 |
| 3.7 | S | C—Br | CH | CH$_2$—CH$_2$ | pyrrolidinyl | 38 |
| 3.8 | S | C—Br | CH | CH$_2$—CH$_2$ | azepanyl | 48 |
| 3.9 | S | C—CH$_3$ | CH | CH$_2$—CH$_2$ | piperidinyl | 43 |
| 3.10 | S | C—CH$_3$ | CH | CH$_2$—CH$_2$ | pyrrolidinyl | 32 |
| 3.11 | S | C—CH$_3$ | CH | CH$_2$—CH$_2$ | azepanyl | 38 |
| 3.12 | CH | C—Cl | S | CH$_2$—CH$_2$ | piperidinyl | 42 |
| 3.13 | C—Br | CH | S | CH$_2$—CH$_2$ | piperidinyl | 37 |
| 3.14 | C—Br | C—Cl | S | CH$_2$—CH$_2$ | piperidinyl | 42 |
| 3.15 | S | C—Cl | CH | CH$_2$—CH$_2$—CH$_2$ | piperidinyl | 48 |

TABLE 3-continued

| Ex. | | | | | | | |
|---|---|---|---|---|---|---|---|
| 3.16 | S | C—Br | CH | CH$_2$—CH$_2$—CH$_2$ | 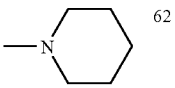 | 62 | |
| 3.17 | CH | C—Cl | S | CH$_2$—CH$_2$—CH$_2$ | 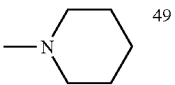 | 49 | |
| 3.18 | CH | C—Br | S | CH$_2$—CH$_2$—CH$_2$ | 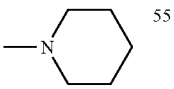 | 55 | |
| 3.19 | S | CH | CH | CH$_2$—CH$_2$—CH$_2$ | 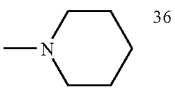 | 36 | |
| 3.20 | S | C—CH$_3$ | CH | CH$_2$ | 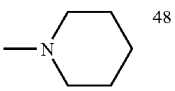 | 48 | |
| 3.21 | CH | —CH$_3$ | S | CH$_2$ | 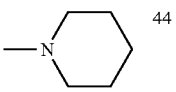 | 44 | |

| Ex. | m.p.: ° C. | Empirical Formula | IR ($\lambda = cm^{-1}$) | $^1$H-NMR δ ppm |
|---|---|---|---|---|
| 3.5 | 228 | C$_{20}$H$_{17}$Cl$_3$N$_4$OS | 3206 (NH), 1651 (C=O); | 1.84-1.96(m, 4 H); 2.94-3.03(m, 6 H); 3.27-3.36(m, 2 H); 5.98(s, 1 H); 7.45-7.46(m, 2 H); 7.56(br s, 1 H, NH exch. with D$_2$O); 7.64(s, 1 H); |
| 3.6 | 181-182 | C$_{22}$H$_{21}$Cl$_3$N$_4$OS | 3224 (NH), 1666 (C=O); | 1.62-1.82(m, 8 H); 2.98(t, 2 H, J = 8.0 Hz); 3.13(t, 4 H, J = 5.8 Hz); 3.30(dt, 2 H, J = 8.0 Hz); 5.98(s, 1 H); 7.44-7.46 (m, 2 H); 7.63(s, 1 H); 8.00(br s, 1 H, NH exch. with D$_2$O); |
| 3.7 | 227 | C$_{20}$H$_{17}$BrCl$_2$N$_4$OS | 3202 (NH), 1650 (C=O); | 1.86-1.93(m, 4 H); 2.93-3.03(m, 6 H); 3.30(dt, 2 H, J = 7.8 Hz); 6.11(s, 1 H); 7.45-7.50(m, 2 H); 7.57(br s, 1 H, NH exch. with D$_2$O); 7.64(s, 1 H); |
| 3.8 | 176 | C$_{22}$H$_{21}$BrCl$_2$N$_4$OS | 3223 (NH), 1666 (C=O); | 1.58-1.78(m, 8 H); 2.99(t, 2 H, J = 8.0 Hz); 3.11-3.16(m, 4 H); 3.29(dt, 2 H, J = 8.0 Hz); 6.11(s, 1 H); 7.44-7.46(m, 2 H); 7.64(s, 1 H); 8.01(br s, 1 H, NH exch. with D$_2$O); |
| 3.9 | 216 | C$_{22}$H$_{22}$Cl$_2$N$_4$OS | 3301 (NH), 1687 (C=O); | 1.42-1.44(m, 2 H); 1.69-1.77(m, 4 H); 2.32(s, CH$_3$); 2.85 (t, 2 H, J = 8.0 Hz); 2.99(t, 2 H, J = 7.4 Hz); 3.28(t, 2 H, J = 8.0 Hz); 5.80(s, 1 H); 7.45(s, 2 H, 1 NH exch. with D$_2$O); 7.61(d, 2 H, J = 9.4 Hz); |
| 3.10 | 235 | C$_{21}$H$_{19}$Cl$_4$N$_2$OS | 3202 (NH), 1652 (C=O); | 1.87-1.91(m, 4 H); 2.32(s, 3 H); 3.00(t, 6 H); 3.29(t, 2 H, J = 7.8 Hz); 5.80(s, 1 H); 7.44-7.45(m, 2 H); 7.56(br s, 1 H, NH exch. with D$_2$O); 7.63(s, 1 H); |
| 3.11 | 229 | C$_{23}$H$_{24}$Cl$_2$N$_4$OS | 3224 (NH), 1664 (C=O); | 1.60-1.80(m, 4 H); 2.32(s, CH$_3$); 2.99(t, 2 H, J = 7.0 Hz); 3.14(t, 4 H, J = 4.8 Hz); 3.28(t, 2 H, J = 7.0 Hz); 5.80(d, 1 H); 7.43-7.44(m, 2 H); 7.63(s, 1 H); 8.02(br s, 1 H, NH exch. with D$_2$O); |
| 3.12 | 232-233 | C$_{22}$H$_{21}$Cl$_3$N$_4$OS | 3201 (NH), 1633 (C=O); | 1.44-1.46(m, 2 H); 1.71-1.78(m, 4 H); 2.82-2.87(m, 4 H); 2.94-2.96(m, 2 H); 3.22-3.33(m, 2 H); 6.90(s, 1 H); 7.41-7.54(m, 2 H); 7.56(br s, 1 H, NH exch. with D$_2$O); 7.60(s, 1 H); |
| 3.13 | 192 | C$_{21}$H$_{19}$BrCl$_2$N$_4$OS | 3318 (NH), 1667 (C=O); | 1.41-1.48(m, 2 H); 1.74-1.77(m, 4 H); 2.81-2.99(m, 4 H); 3.26-3.37(m, 2 H); 7.05(s, 1 H); 7.40-7.49(m, 2 H); 7.58(br s, 1 H, NH exch. with D$_2$O); 7.63(s, 1 H); |
| 3.14 | 235 | C$_{21}$H$_{18}$BrCl$_3$N$_4$OS | 3318 (NH), 1667 (C=O); | 1.42-1.45(m, 2 H); 1.72-1.77(m, 4 H); 2.82-2.88(m, 4 H); 2.94-2.96(m, 2 H); 3.24-3.35(m, 2 H); 7.41-7.51(m, 2 H); 7.56(br s, 1 H, NH exch. with D$_2$O); 7.65(s, 1 H); |
| 3.15 | 222-224 | C$_{22}$H$_{21}$Cl$_3$N$_4$OS | 3383 (NH), 1971 (C=O); | 1.43-1.47(m, 2 H); 1.73-1.76(m, 4 H); 2.80-2.91(m, 4 H); 2.94-2.96(m, 2 H); 3.21-3.32(m, 2 H); 6.70(s, 1 H); 7.40-7.52(m, 2 H); 7.57(br s, 1 H, NH exch. with D$_2$O); 7.65(s, 1 H); |
| 3.16 | 212 | C$_{22}$H$_{21}$BrCl$_2$N$_4$OS | 3377 (NH), 1682(C=O); | 1.42-1.47(m, 2 H); 1.71-1.74(m, 6 H); 2.81-2.91(m, 4 H); 2.95-3.00(m, 2 H); 3.21-3.32(m, 2 H); 6.81(s, 1 H); 7.42-7.56(m, 2 H); 7.58(br s, 1 H, NH exch. with D$_2$O); 7.61(s, 1 H); |
| 3.17 | 226 | C$_{22}$H$_{21}$Cl$_3$N$_4$OS | 3371 (NH), 1680 (C=O); | 1.39-1.44(m, 2 H); 1.70-1.74(m, 6 H); 2.78-2.87(m, 4 H); 2.90-2.93(m, 2 H); 3.20-3.29(m, 2 H); 6.84(s, 1 H); 7.40-7.51(m, 2 H); 7.58(br s, 1 H, NH exch. with D$_2$O); 7.66(s, 1 H); |

TABLE 3-continued

| | | | | |
|---|---|---|---|---|
| 3.18 | 215 | $C_{22}H_{21}BrCl_2N_4OS$ | 3393 (NH), 1682 (C=O); | 1.41-1.45(m, 2 H); 1.71-1.75(m, 6 H); 2.80-2.91(m, 4 H); 2.95-2.98(m, 2 H); 3.21-3.30(m, 2 H); 6.78(s, 1 H); 7.44-7.51(m, 2 H); 7.60(br s, 1 H, NH exch. with $D_2O$); 7.68(s, 1 H); |
| 3.19 | 179-181 | $C_{22}H_{22}Cl_2N_4OS$ | 3163 (NH), 1650 (C=O); | 1.37-1.50(m, 2 H); 1.65-1.70(m, 4 H); 2.05-2.20 (m, 2 H); 2.78-2.92(m, 4 H); 2.95-3.08(m, 2 H); 3.23-3.38(m, 2 H); 6.13(d, 1 H, J = 5.4 Hz); 6.83 (d, 1 H, J = 5.4 Hz); 7.35-7.45(m, 2 H); 7.54(s, 1 H); 7.64(br s, 1 H, NH exch. with $D_2O$); |
| 3.20 | 222-224 | $C_{21}H_{20}Cl_2N_4OS$ | 3369 (NH), 1673 (C=O); | 1.44-1.47(m, 2 H); 1.69-1.75(m, 4 H); 2.32(s, $CH_3$); 2.85-2.94(m, 4 H); 3.80(s, 2 H); 6.68(s, 1 H); 7.42-7.55(m, 2 H); 7.59(br s, 1 H, NH exch. with $D_2O$); 7.67(s, 1 H); |
| 3.21 | 213-215 | $C_{21}H_{20}Cl_2N_4OS$ | 3402 (NH), 1684 (C=O); | 1.41-1.44(m, 2 H); 1.65-1.70(m, 2 H); 2.28(s, $CH_3$); 2.81-2.89(m, 4 H); 3.78(s, 2 H); 6.65(s, 1 H); 7.44-7.52(m, 2 H); 7.57(br s, 1 H, NH exch. with $D_2O$); 7.62(s, 1 H); |

Example 4

Affinity Towards the Cannabinoidergic CB1 and CB2 Receptors

The affinity of the synthesized compounds towards the cannabinoidergic CB1 and CB2 receptors was evaluated in vitro through radioreceptorial binding studies by utilizing the following method.

The receptorial binding technique allows indeed to establish if and with what affinity and specificity a determined compound binds itself to a particular receptor. To evaluate the possible affinity of a determined compound towards a particular receptor it is necessary to make to compete (in a particular preparation of the tissue in which those determined receptors are present) the compound to be tested with another compound whose affinity is known and whose molecule was rendered radioactive. The capability of the compound to be tested to remove the radioactive compound gives an index of the affinity by which the compound binds itself to that determined receptor. The reading of the radioactivity present in the receptor-compound complex allows furthermore to calculate with extreme precision the amount of compound bound to the receptor. By this method it is therefore possible to quickly identify the affinity of a new compound towards a specific receptor and to be able to make predictions on its pharmacological activity. By repeating the same experimental scheme it is possible to evaluate the affinity of the compound towards other kinds of receptors and establish then the specificity degree.

The receptorial binding technique, besides being used for the screening of new molecules having a pharmacological activity, can give useful information relating to possible changes at receptorial level related for example to a prolonged exposure to drugs and/or particular pathologies. As a matter of fact, in these situations, changes in the amount of the receptors present or structural changes can be pointed out altering the agonist or antagonist affinity with repercussions on the normal function of the receptors themselves.

The experimentation was carried out according to the guide lines of the European Community for the animal experimentation (EEC No. 86/609), by employing laboratory animals (rats) housed in groups of twenty for cage, under standard stalling conditions (temperature 22±2° C., relative humidity 60%, artificial lighting with a 12 hour light-dark cycle). Food and water were available ad libitum.

The procedure used, based on the employment of the compound [$^3$H]-CP-55,940 (New England Nuclear, Boston, Mass., USA), requires the utilization of rat brain as biological tissue for the evaluation of the affinity towards the CB1 receptors and of rat spleen for the affinity determination towards the CB2 receptors.

The animals were sacrificed by cervical dislocation, the brain in toto (cerebellum excluded) and the spleen were rapidly dissected and maintained in ice.

The tissue was homogenized in 15 volumes (weight/volume) of TME buffer (50 mM Tris, 1 mM EDTA e 3 mM $MgCl_2$, pH 7.4) by an Ultra-Turrax and centrifuged for 10 minutes at 1086×g in a centrifuge cooled at 4° C. The resulting supernatant was centrifuged at 45,000×g for 30 min at 4° C. by using a Beckman SW41 rotor and the final pellet was resuspended in 50 volumes of TME.

The obtained membranes (50-80 μg of proteins) were incubated in the presence of 1 nM di[$^3$H]-CP55,940 for 1 h at 30° C. in a final volume of 0.5 ml of TME buffer containing 5 mg/ml of bovine serum albumin (BSA). The non specific binding was measured in the presence of CP55,940 at the 1 μM concentration.

All the experiments were carried out in polypropylene test tubes pretreated with Sigma-Cote (Sigma Chemical Co. Ltd., Poole, UK) to reduce the non specific binding.

For the building of the competitive inhibition binding curves eight different concentrations of each compound were used. As reference compounds SR141716A for the CB1 receptors and SR144528 for the CB2 receptors were utilized.

Incubation was interrupted by addition of TME buffer (at 4° C.) containing 5 mg/ml of BSA and filtration under vacuum through Whatman GFC filters pretreated with 0.5% of polyethylamine (PEI) and by using a filtering apparatus (Brandell, Gaithersburg, Md., USA). Filters were washed 3 times with 5 ml of Tris HCl buffer (pH 7.4, 4° C.) containing 1 mg/ml of BSA and singly placed in plastic vials containing 4 ml of scintillating liquid (Ultima Gold MV, Packard).

The radioactivity present in the filters was measured by a scintillator spectrophotometer (Tricarb 2100, Packard, Meridien, USA).

The protein determination was carried out by the Bradford method by using the protocol and the reactants supplied by Bio-Rad (Milano, Italia).

The experiments were carried out in triplicate and the results confirmed in five independent experiments.

The affinity of the compounds towards the CB1 and CB2 receptors was expressed in Ki terms.

Table 4 shows the Ki values obtained with the compounds of the present invention examined in the test in vitro. The affinity of the compounds object of the present invention is compared with that relating to the reference compounds SR144528 and SR141716A (Rimonobant®).

The Table shows that the compounds of the present invention have activity on the CB1 and/or CB2 receptors comparable with that of the prior art compounds active on said receptors.

Example 5

Hypothermia Tests In Vivo

As said, the compounds having cannabimimetic activity show in vivo the following effects: hypoactivity, hypothermia, analgesia and catalepsy (B. R. Martin et al., *Pharmacol. Biochem. Behav.;* 1991, 40, 471-478; P. B. Smith et al.; *J. Pharmacol. Exp. Ther.;* 1994, 270, 219-227). To be able to exert the thermoregulation function, the compounds having activity towards the cannabinoidergic receptors must be capable to pass the hemato-encephalic barrier, the central site of said receptors regulating the temperature being positioned in the preoptical front nucleus of the hypothalamus (S. M. Rawls et al.; *J. Pharmacol. Exp. Ther.;* 2002, 303, 395-402). Following treatments with CB1 agonist compounds capable to pass the hemato-encephalic barrier, the cannabimimetic activity is pointed out itself by the recording of a body temperature reduction. In case of CB1 antagonist compounds capable to pass the hemato-encephalic barrier, the treatment with said compounds does not imply any body temperature variation, however it implies an antagonist activity towards reference CB1 agonists as WIN 55,212-2, thus contrasting the hypothermia induced by the latter.

To evaluate the capability of the compounds of general formula (I) in passing the hemato-encephalic barrier, tests were then carried out directed to the evaluation of hypothermia induced as a result of treatments carried out with said compounds. Tests were carried out in the experiment animal (rat) according to the work indications by M. Rinaldi-Carmona et al. in *FEBS Letters;* 1994, 350, 240-244. The rectal temperature in the rat was determined by an electronic thermometer inserted at a 2 mm depth. The measurements were carried out on rats acclimated for one hour. The rectal temperature was determined before and after (from 30 to 120 minutes) the i.p. administration of the compound to be tested.

When no temperature reduction following the administration of the compound to be tested was pointed out, it was evaluated the passage of the hemato-encephalic barrier by evaluating the possible antagonist activity of the same towards a reference CB1 agonist compound as WIN 55,212-2. For this purpose the rectal temperature measurements were carried out upon i.p. administration of the compound to be tested 30 minutes before the WIN 55,212-2 administration. The compounds capable to pass the hemato-encephalic barrier and to antagonise the CB1 agonist activity of WIN 55,212-2 are indeed capable to contrast the temperature reduction induced by the reference agonist.

Each test was repeated on ten animals; the reported results are the average of the results obtained with the ten animals.

The Examples reported hereinafter show that the invention compounds (I) (Examples from 5.1 to 5.4), having affinity towards the CB1 receptors as it has been shown in the tests in vitro of the Examples 4, are unable to pass the hemato-encephalic barrier, said compounds being indeed unable to induce hypothermia or to contrast the temperature reduction induced by the CB1 agonist compound WIN 55,212-2.

The behaviour of the compounds of general formula (I) is completely different from that of the reference compound SR 141716A, which is on the contrary capable to pass the hemato-encephalic barrier, antagonizing the hypothermia induced by WIN 55,212-2 (comparative Example 5.5).

Example 5.1

The test was carried out with the compound of the Example 3.2. Aqueous samples were used wherein the compound of the Example 3.2 was dispersed in water with three drops of Tween 80. Following the above procedure, treatments were carried out with doses (mg compound/kg of body weight) of 0.1; 0.5; 1.0; 3.0; 30.0.

In none of the examined cases there was a reduction of the body temperature in the treated rats with respect to the physiological solution administration (38° C.). Also in case of the evaluation of the antagonist activity towards WIN 55,212-2 (3 mg compound/kg of body weight), no variation of the body temperature with respect to the treatment with the only WIN 55,212-2 was noticed.

The temperatures detected during the experiment, from the zero time (i.p. administration) up to 120 min are reported in Table 5.

Example 5.2

The Example 5.1 was repeated but with the compound of the Example 3.5 instead of that of the Example 3.2.

As in case of the compound of the Example 3.2, also the compound of the Example 3.5 was not able to pass the hemato-encephalic barrier, said compound being unable to induce hypothermia or to contrast the temperature reduction induced by the CB1 agonist compound WIN 55,212-2.

With no dose employed a reduction of the body temperature in the treated rats was indeed noticed. Also in case of the evaluation of the antagonist activity towards WIN 55,212-2, no variation of the body temperature with respect to the treatment with only WIN 55,212-2 was noticed.

Example 5.3

The Example 5.1 was repeated but by using the compound of the Example 3.6 instead of that of the Example 3.2; as in case of the compound of the Example 5.1, also the compound of the Example 3.6 was unable to pass the hemato-encephalic barrier, said compound being unable to induce hypothermia or to oppose the temperature reduction induced by the CB1 agonist compound WIN 55,212-2.

With none of the doses employed a reduction of the body temperature in the treated rats was indeed noticed.

Also in case of the evaluation of the antagonist activity towards WIN 55,212-2, no variation of the body temperature with respect to the treatment with the only WIN 55,212-2 was noticed.

Esempio 5.4

The Example 5.1 was repeated but with the compound of the Example 3.9 instead of that of the Example 3.2.

As in case of the compound of the Example 5.1, also the compound of the Example 3.9 was unable to pass the hemato-encephalic barrier, said compound being unable to induce hypothermia or to oppose the temperature reduction induced by the CB1 agonist compound WIN 55,212-2.

With none of the doses employed a reduction of the body temperature in the treated rats was indeed noticed.

Also in case of the evaluation of the antagonist activity towards WIN 55,212-2, no variation of the body temperature with respect to the treatment with the only WIN 55,212-2 was noticed, Example 5.5

Comparative

The Example 5.1 was repeated but by using the reference CB1 antagonist compound SR141716A instead of the compound of the Example 3.2.

The CB1 antagonist SR141716A, as such, has not implied any variation of the body temperature in the treated rats, however it was able to antagonize the effect of WIN 55,212-2, as shown in Table 6.

The results of the Table show that differently from the compounds of formula (I) object of the present invention, the reference compound SR 141716A is capable to pass the hemato-encephalic barrier since it is able to oppose the hypothermia induced by the CB1 agonist WIN 55,212-2.

Example 6

Intestinal Motility Tests

To evaluate the activity in vivo of the compounds (I) object of the present invention, functional tests were carried out directed to the evaluation of the effect of said compounds on the rat intestinal motility. It was indeed shown the involvement of the cannabinoidergic CB1 receptors in the intestinal motility regulation in rat (R. G. Pertwee et al; *Br. J. Pharmacol.*; 1996, 118, 2199-2205). In particular, the CB1 receptor agonists slacken the gastrointestinal motility; antagonist compounds of the same receptors have instead a prokinetic effect on the gastrointestinal transit (G. Colombo et al.; *Eur. J. Pharmacol.*; 1998, 344, 67-69; M. A. Casu et al.; *Eur. J. Pharmacol.*; 2003, 459, 97-105).

The evaluation of the constipating or prokinetic effect of the compounds was carried out by the *Upper Gut Transit Test* method on the basis of the procedure defined and ratified by Y. Nagakura et al.; *Eur. J. Pharmacol.*; 1996, 311, 67-72. The method, which allows to measure the motility of the stomach and of the first intestine tract (small or little intestine), requires:
- the administration of the compound to be tested by i.p. route;
- the administration of carmine red (marker not directly absorbable from the stomach) by intragastric route through a metal probe, after 20 minutes from the administration of the compound to be tested;
- the rat sacrifice by cervical dislocation after a pre-fixed time (30 minutes) starting from the administration time;
- the intestine explant from pylorus to the ileo-cecal valve;
- the determination of the intestinal part crossed by the marker;
- the data processing to determine the percentage of crossed part with respect to the total length of the small intestine.

With respect to the control (physiological solution or carrier wherein the compounds to be tested were solubilized or dispersed), the administration of CB1 agonist compounds implies an intestinal transit percentage reduction; an opposite effect is noticed in case of antagonist compounds. The latter are therefore capable to cancel the constipating effect of CB1 agonist compounds.

Each test was repeated on ten animals; the results reported in the Examples are the average of the results obtained with ten animals.

The Examples reported hereinafter show that the invention compounds (I) are active on the gastrointestinal tract. In particular the compounds of formula (I) of the Examples 6.1 and 6.2 increase the intestinal transit rate and are capable to antagonize the effect of a CB1 agonist as the compound WIN 55,212-2, implying a prokinetic effect on the gastrointestinal tract. The observed effect is comparable with that of the reference compound SR 141716A (comparative Example 6.3). Differently from the reference compound, which, as shown above by the hypothermia tests, is capable to pass the hemato-encephalic barrier, the formula (I) compounds of the present invention (Examples 6.1 and 6.2) have affinity towards the cannabinoidergic CB1 receptors, are able to influence the intestinal motility, but are unable to pass the hemato-encephalic barrier (see the Examples 5.1 and 5.2). Such compounds are therefore new potential active principles to be used in the treatment of gastrointestinal tract pathologies, without these can cause any side effect on the central nervous system. The results obtained with these Examples allow a general extrapolation towards all the peripheral system pathologies wherein the modulation of the cannabinoidergic CB1 or CB2 receptors is implied.

Example 6.1

The test was carried out with the compound of the Example 3.5; aqueous samples were in particular used wherein the compound 3.5 was dispersed in water with three drops of Tween 80. According to the above procedure, with treatments equal to 5 mg of compound/kg of body weight, the marker has run on an average an intestinal portion equal to 67% with respect to the total intestine length, while following the administration of a physiological solution containing the same amount of Tween 80, the marker has run on an average an intestinal portion equal to 50%.

The prokinetic effect of the compound of the Example 3.5 was evaluated also towards the constipating action of the CB1 agonist compound WIN 55,212-2. The treatment of rats with aqueous samples of WIN 55,212-2 with concentrations equal to 0.5 mg of compound/kg of body weight, has implied a covering of the intestinal transit from the marker equal to 25% of the total of the intestine with respect to the total length. In case of similar treatment with WIN 55,212-2 preceded by the administration of an aqueous sample of the compound of the Example 3.5 with concentration equal to 1.5 mg of compound/kg of body weight, the marker has instead run, on an average, the 50% with respect to the total length of the intestine.

Example 6.2

The Example 6.1 was repeated but by using the compound of formula (I) of the Example 3.6 instead of the compound of the Example 3.5. Furthermore in this Example the doses of the treatment were changed in function of the Ki values determined in the Example 4. With treatments equal to 1 and 5 mg of compound/kg of body weight, respectively, the marker has run on an average an intestinal portion equal to 65% and to 75%, respectively, with respect to the total length of the intestine, while following the administration of physiological solution containing the same amount of Tween 80, the marker has run on an average an intestinal portion equal to 50%.

Also in this case the prokinetic effect of the compound of the Example 3.6 was evaluated towards the constipating action of the CB1 agonist compound WIN 55,212-2. The rat treatment with aqueous samples of WIN 55,212-2 with concentrations equal to 0.5 mg of compound/kg of body weight, has implied a covering of the intestinal transit from the marker equal to 25% of the total of the intestine with respect to the total length. In case of similar treatment with WIN 55,212-2 preceded by the administration of an aqueous sample of the compound of the Example 3.6 with concentration equal to 0.3 mg of compound/kg of body weight, the marker has instead run on an average the 50% with respect to the total intestine length.

Example 6.3

Comparative

The Example 6.1 was repeated but by using the reference compound SR 141716A at the place of the compound of the Example 3.5; furthermore the doses of the treatment were changed in function of the Ki values determined in the Example 4. With treatments equal to 2.5 mg of compound/kg of body weight, the marker has run on an average an intestinal portion equal to 75% with respect to the total intestine length, while following the administration of physiological solution containing the same amount of Tween 80, the marker has run on an average an intestinal portion equal to 50%.

The treatment of rats with aqueous samples of WIN 55,212-2 with concentrations equal to 0.5 mg of compound/kg of body weight, has implied a covering of the intestinal transit from the marker equal to 25% of the total of the intestine with respect to the total length. In the case of similar treatment with WIN 55,212-2 preceded by the administration of an aqueous sample of the reference compound SR 141716A with concentration equal to 0.1 mg of compound/kg of body weight, the marker has instead run on an average the 50% with respect to the total length of the intestine.

TABLE 4

Activity in vitro of the invention compounds on the CB1 and CB2 receptors

| Compound (Ex.) | CB1 (brain) Ki (nM) | CB2 (spleen) Ki (nM) |
|---|---|---|
| 3.1 | 44.3 ± 0.5 | 67.4 ± 6 |
| 3.2 | 4.47 ± 0.14 | 36.75 ± 5 |
| 3.5 | 137 ± 12 | 243 ± 14 |
| 3.6 | 9.83 ± 0.72 | 20.81 ± 1.4 |
| 3.7 | 126 ± 5 | 195 ± 27 |
| 3.8 | 9.6 ± 1.7 | 60.01 ± 1 |
| 3.9 | 7.88 ± 0.5 | 55.15 ± 6 |
| 3.11 | 57 ± 6 | 57.1 ± 5 |
| SR144528 (comp) | 70 ± 10 | 0.28 ± 0.04 |
| SR141716A (comp) | 1.8 ± 0.075 | 514 ± 30 |

TABLE 5

Pharmacological Example 5.1: trend of the body temperature after administration in rat (10 animals) of the compounds indicated in the Table.

| | Body temperature (° C.) | | |
|---|---|---|---|
| Time from the administration (minutes) | WIN 55,212-2 (3 mg/kg) | Compound Ex. 3.2 (0.1-30 mg/kg) | WIN 55,212-2 (3 mg/kg) + compound Ex. 3.2 (0.1-30 mg/kg) |
| 0 | 37.9 | 38.0 | 38.0 |
| 15 | 35.6 | 37.9 | 38.0 |
| 30 | 33.8 | 38.0 | 34.0 |
| 60 | 34.5 | 38.2 | 34.5 |
| 90 | 35.8 | 38.1 | 35.8 |
| 120 | 36.8 | 37.9 | 36.8 |

WIN 55,212-2 is a CB1 agonist compound which passes the hematoencephalic barrier and reduces the body temperature. The animal body temperature after administration of a physiological solution is on an average of 38° C.

TABLE 6

Pharmacological Example 5.5 (comparative): trend of the body temperature after administration in rat (10 animals) of the compounds indicated in the Table.

| | Body Temperature (° C.) | | |
|---|---|---|---|
| Time from the administration (minutes) | WIN 55,212-2 (3 mg/kg) | WIN 55,212-2 (3 mg/kg) + SR141716A (0.1 mg/kg) | WIN 55,212-2 (3 mg/kg) + SR141716A (0.5 mg/kg) |
| 0 | 37.9 | — | — |
| 15 | 35.6 | — | — |
| 30 | 33.8 | 35.3 | 37.0 |
| 60 | 34.5 | 36.9 | 37.8 |
| 90 | 35.8 | 37.5 | 37.9 |
| 120 | 36.8 | — | — |

WIN 55,212-2 is a CB1 agonist compound which passes the hematoencephalic barrier and reduces the body temperature; SR141716A is a CB1 antagonist compound which passes the hematoencephalic barrier and which does not cause variation of the body temperature in the treated rats. The animal body temperature after administration of a physiological solution is on an average of 38° C.

What is claimed is:

1. A compound of the chemical structure (I):

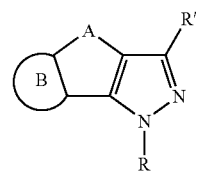

(I)

wherein:
A is $(CH_2)_t$ wherein
t is equal to 1, 2 or 3;
B is an heteroaryl with a ring having 5 or 6 atoms, selected from the following:
thiophene, furan, oxazole, thiazole, imidazole, isoxazole, isothiazole, triazole, pyridazine, pyrazine, triazine, or pyrrole, optionally substituted with a number of substituents from 1 to 4, said substituents being equal to or different from each other and selected from the following: halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, isothiocyanate, phenyl, cycloalkyl, saturated or unsaturated heterocycle, or heteroaryl;

R is
a linear or branched $C_1$-$C_{10}$ alkyl, wherein the end of the main chain not linked to the nitrogen atom has —$CH_2$—W termination, W being a group selected from hydrogen, halogen, isothiocyanate, CN, OH, $OCH_3$, $NH_2$, or —$CH=CH_2$; or an aryl, arylalkyl or arylalkenyl, not substituted or having from one to five substituents, equal to or different from each other, selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, a saturated or unsaturated heterocycle, or phenyl; and R' is
a ketonic group of formula —C(O)—Z', wherein Z' is a $C_1$-$C_8$ alkyl or a $C_3$-$C_{15}$ cycloalkyl, a saturated or unsaturated heterocycle, an aryl, or a heteroaryl; or an amidic substituent of formula —C(O)—NH-T', wherein T' is selected from:
$C_1$-$C_8$ alkyl;
$C_1$-$C_7$ haloalkyl;
an aryl, arylalkyl or arylalkenyl, optionally containing one heteroatom selected from S, N, or O, either not substituted or optionally having from one to four substituents, equal to or different from each other, said substituents selected from halogen, $C_1$-$C_7$ alkyl, $C_1$-$C_7$ haloalkyl, $C_1$-$C_7$ haloalkoxy, $C_1$-$C_7$ alkylthio, or $C_1$-$C_7$ alkoxy;
a $C_3$-$C_{15}$ cycloalkyl either not substituted or substituted with one or more $C_1$-$C_7$ alkyl chains, said chains being from one to four chains for $C_5$-$C_{15}$ cycloalkyls, one to three chains for $C_4$ cycloalkyl, and being from one to two chains for $C_3$ cycloalkyl, said alkyl chains being equal to or different from each other;
a group of formula (IA):

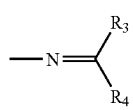

(IA)

wherein $R_3$ and $R_4$ are equal to or different from each other and are hydrogen or $C_1$-$C_3$ alkyl, with the proviso that $R_3$ and $R_4$ are not both hydrogen;
a group of formula (IB):

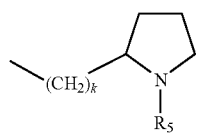

(IB)

wherein $R_5$ represents a $C_1$-$C_3$ alkyl and k is an integer between 1 and 3 or
a group $NR_1R_2$, wherein $R_1$ and $R_2$ are equal or different and are
hydrogen;
a $C_1$-$C_7$ alkyl; or
an aryl, arylalkyl or arylalkenyl not substituted or optionally having on the aromatic rings from one to five substituents, equal to or different from each other, selected from halogen, $C_1$-$C_7$ alkyl, $C_1$-$C_7$ haloalkyl, $C_1$-$C_7$ haloalkoxy, $C_1$-$C_7$ alkylthio, or $C_1$-$C_7$ alkoxy; or $R_1$ and $R_2$ together with the nitrogen atom to which they are linked form a, saturated or unsaturated, heterocycle from 5 to 10 atoms, either not substituted or optionally having from one to four substituents, equal to or different from each other, selected from the group consisting of: $C_1$-$C_7$ alkyl, phenyl and benzyl, said phenyl or benzyl substituted with one or more groups, equal to or different from each other, selected from: halogen, $C_1$-$C_7$ alkyl, $C_1$-$C_7$ haloalkyl, haloalkoxy, alkylthio, and $C_1$-$C_7$ alkoxy;

or pharmaceutically acceptable salts or reactive derivatives thereof selected from acyl halides, anhydrides, mixed anhydrides, imidazolides, ester-amide adducts, or linear or branched $C_1$-$C_4$ alkyl esters, thereof.

2. The compound of claim 1, wherein:
A is —$(CH_2)_t$—, wherein t is defined as in claim 1;
B is optionally substituted with a number of substituents from 1 to 4, said substituents being equal to or different from each other and selected from the following: halogen, $C_1$-$C_7$ alkyl, $C_1$-$C_7$ alkylthio, $C_1$-$C_7$ alkoxy, $C_1$-$C_7$ haloalkyl, and $C_1$-$C_7$ haloalkoxy;
R is a linear or branched $C_1$-$C_{10}$ alkyl, wherein the end not linked to the nitrogen atom of the main chain has —$CH_2$—W termination, wherein W is a halogen;
an arylalkyl or an arylalkenyl not substituted or having from one to five substituents, equal to or different from each other, said substituents selected from halogen, $C_1$-$C_7$ alkyl, $C_1$-$C_7$ alkylthio, $C_1$-$C_7$ alkoxy, $C_1$-$C_7$ haloalkyl, $C_1$-$C_7$ haloalkoxy, cyano, nitro, amino, N-alkylamino, N,N-dialkylamino, saturated or unsaturated heterocycle, or phenyl;
R' is a ketonic group of formulae —C(O)—Z', wherein Z' is as defined as in claim 1, or an amide of formula —C(O)—NH-T' wherein T' is as defined as in claim 1 excluding the formulas (IA) and (IB).

3. The compound of claim 1, wherein:
A is —$(CH_2)_t$—, wherein t is defined as in claim 1;
B is optionally substituted with one, two, three or four substituents, said substituents equal to or different from each other, selected from:
halogen, $C_1$-$C_3$ alkyl, $C_1$-$C_3$ alkylthio, $C_1$-$C_3$ alkoxy, $C_1$-$C_3$ haloalkyl, or $C_1$-$C_3$ haloalkoxy;
R has the following meanings:
linear or branched $C_1$-$C_7$ alkyl, wherein the end not linked to the nitrogen atom of the main chain has —$CH_2$—W termination, wherein W is a halogen;
an arylalkyl or arylalkenyl, not substituted or having from one to five substituents, equal to or different from each other, selected from halogen, $C_1$-$C_3$ alkyl, $C_1$-$C_3$ alkylthio, $C_1$-$C_3$ alkoxy, $C_1$-$C_3$ haloalkyl, or $C_1$-$C_3$ haloalkoxy;
R' is
a ketonic group of formulae —C(O)—Z', wherein Z' is as defined as in claim 1, or an amide of formula —C(O)—NH-T'; wherein T' is a group selected from the following:
$C_1$-$C_8$ alkyl;
$C_1$-$C_7$ haloalkyl;
an aryl, arylalkyl or arylalkenyl, optionally containing one heteroatom, not substituted or having from one to five substituents, equal to or different from each other, selected from halogen, $C_1$-$C_3$ alkyl, $C_1$-$C_3$ haloalkyl, $C_1$-$C_3$ haloalkoxy, $C_1$-$C_3$ alkylthio, or $C_1$-$C_3$ alkoxy;

an $NR_1R_2$ group, wherein $R_1$ and $R_2$ are as defined as in claim 1, and a $C_3$-$C_{15}$ cycloalkyl not substituted or substituted with one or more $C_1$-$C_7$ alkyl chains, said chains being from one to four chains for $C_5$-$C_{15}$ cycloalkyls, being from one to three chains for the $C_4$ cycloalkyl, and being from one to two chains for the $C_3$ cycloalkyl, said alkyl chains being equal to or different from each other.

4. The compound of claim 1, wherein R'=—C(O)—NHT'.

5. The compound of claim 1, wherein the structure of the compound is chiral.

6. The compound of claim 1, wherein the compound is a cis-trans isomer.

7. A pharmaceutical composition comprising the compound of claim 1 and pharmaceutically acceptable additives or excipients.

8. A pharmaceutical composition comprising the compound of claim 1, further comprising additives or excipients which allow the compound of claim 1 to pass the hematoencephalic barrier.

9. The pharmaceutical composition of claim 7, wherein the additives or excipients comprise sodium alkyl sulfate.

10. A pharmaceutical composition comprising from about 0.5 to about 20% by weight of the compound of claim 1, from about 0.05 to about 0.5% by weight of sodium alkyl sulfate and from about 2.5 to about 10% by weight of a disintegrating agent.

11. A compound of the chemical structure and corresponding geometric isomers and stereoisomers:

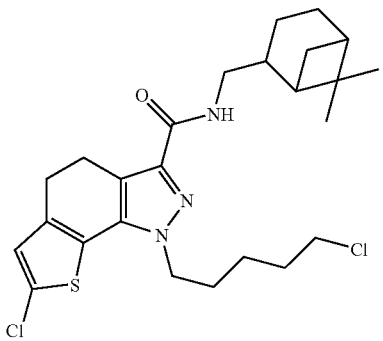

or pharmaceutically acceptable salts thereof.

12. The compound of claim 1, wherein B is a thiophene.

13. The compound of claim 1, wherein t is 1.

14. The compound of claim 1, wherein t is 2.

15. The compound of claim 1, wherein t is 3.

16. The compound of claim 1, wherein R' is —C(O)—NH-T', wherein T' is a $C_3$-$C_{15}$ cycloalkyl either not substituted or substituted with one or more $C_1$-$C_7$ alkyl chains, said chains being from one to four chains for $C_5$-$C_{15}$ cycloalkyls, being from one to three chains for $C_4$ cycloalkyl, and being from one to two chains for $C_3$ cycloalkyl, said alkyl chains being equal to or different from each other.

* * * * *